(12) United States Patent
Seeney et al.

(10) Patent No.: US 10,220,164 B2
(45) Date of Patent: Mar. 5, 2019

(54) DELIVERY DEVICES

(75) Inventors: Philip Seeney, Cambridge (GB);
Douglas Ivan Jennings, Royston (GB)

(73) Assignee: Pharmaxis Ltd., New South Wales (AU)

( * ) Notice: Subject to any disclaimer, the term of this patent is extended or adjusted under 35 U.S.C. 154(b) by 277 days.

(21) Appl. No.: 14/232,503

(22) PCT Filed: Jul. 13, 2012

(86) PCT No.: PCT/GB2012/051684
§ 371 (c)(1),
(2), (4) Date: Jan. 13, 2014

(87) PCT Pub. No.: WO2013/008037
PCT Pub. Date: Jan. 17, 2013

(65) Prior Publication Data
US 2014/0174441 A1 Jun. 26, 2014

(30) Foreign Application Priority Data

Jul. 13, 2011 (GB) .................................... 1112031.8
Jul. 22, 2011 (GB) .................................... 1112668.7

(51) Int. Cl.
*A61M 15/00* (2006.01)
*A61M 15/08* (2006.01)

(52) U.S. Cl.
CPC ...... *A61M 15/003* (2014.02); *A61M 15/0003* (2014.02); *A61M 15/0008* (2014.02);
(Continued)

(58) Field of Classification Search
CPC .............. A61M 15/00; A61M 15/0001; A61M 15/0028; A61M 15/0063; A61M 15/0086; A61M 15/0088
See application file for complete search history.

(56) References Cited

U.S. PATENT DOCUMENTS 4,069,819 A   1/1978  Valentini et al.
4,210,140 A * 7/1980  James ............... A61M 15/0028
                                                    604/58
(Continued)

FOREIGN PATENT DOCUMENTS

EP   1329236 A1   7/2003
WO   9826828 A2   6/1998
(Continued)

OTHER PUBLICATIONS

EP Examination Report, dated Jan. 5, 2016 from EP Application No. 12 740 193.3, 2 pgs.

*Primary Examiner* — Gregory A Anderson
*Assistant Examiner* — Victoria Murphy
(74) *Attorney, Agent, or Firm* — Young Basile Hanlon & MacFarlane, P.C.

(57) ABSTRACT

A delivery device is provided which has a container containing a dose of a powder, a chamber adapted to receive the container, at least one gas inlet by which gas may enter the chamber, and at least one gas outlet by which gas and entrained powder may exit the chamber for inhalation. The delivery device has a pre-use configuration in which the container is accommodated, at least partially, within a storage enclosure in a wall of the chamber. The delivery device has a deployment member adapted to put the delivery device in an operative configuration by displacing the container from the storage enclosure into the chamber, such that the container is movable within the chamber, in use, the deployment member being adapted to at least partially occupy the storage enclosure in the operative configuration.

25 Claims, 15 Drawing Sheets

(52) U.S. Cl.
CPC .... *A61M 15/0021* (2014.02); *A61M 15/0023* (2014.02); *A61M 15/0028* (2013.01); *A61M 15/0043* (2014.02); *A61M 15/08* (2013.01); *A61M 2202/064* (2013.01); *A61M 2206/16* (2013.01)

(56) References Cited

U.S. PATENT DOCUMENTS

| | | | |
|---|---|---|---|
| 4,353,365 A * | 10/1982 | Hallworth | A61M 15/0028 128/203.15 |
| 5,787,881 A | 8/1998 | Chawla | |
| 6,705,313 B2 | 3/2004 | Niccolai | |
| 6,715,486 B2 | 4/2004 | Gieschen et al. | |
| 7,305,986 B1 | 12/2007 | Steiner et al. | |
| 2001/0027790 A1 | 10/2001 | Gieschen et al. | |
| 2002/0158150 A1 | 10/2002 | Matsugi et al. | |
| 2004/0025876 A1 | 2/2004 | Miller et al. | |
| 2004/0206350 A1 | 10/2004 | Alston et al. | |
| 2004/0208832 A1 | 10/2004 | Bates | |
| 2007/0283955 A1 | 12/2007 | Tsutsui | |
| 2009/0209502 A1 | 8/2009 | Haeberlin et al. | |
| 2010/0300441 A1 * | 12/2010 | Von Schuckmann | A61M 15/0065 128/203.15 |
| 2012/0216805 A1 * | 8/2012 | Brunnberg | A61M 11/06 128/203.12 |

FOREIGN PATENT DOCUMENTS

| | | | | |
|---|---|---|---|---|
| WO | | 02085281 A1 | 10/2002 | |
| WO | | 03075988 A1 | 9/2003 | |
| WO | | 2008001132 A1 | 1/2008 | |
| WO | WO | 2008001132 A1 * | 1/2008 | ........ A61M 15/0028 |

* cited by examiner

DELIVERY DEVICES

CROSS REFERENCE TO RELATED APPLICATION

The present application claims priority to Great Britain Patent Application Nos. 1112031.8, filed Jul. 13, 2011 and 1112668.7, filed Jul. 22, 2011, each incorporated herein in its entirety.

TECHNICAL FIELD

This invention relates to delivery devices, and in particular delivery devices in which a container is provided within a chamber, and gas flow through the chamber causes powder to be dispensed from the container.

Administration of powdered medicaments by inhalation is frequently carried out with dry powder delivery devices (DPIs). In conventional DPIs, the powdered medicament is held in either manually-loaded single-dose capsules or blisters, which must be pierced, punctured or opened to release the dose, or a large multi-dose powder reservoir within the device from which medicament is dispensed by manually actuating a dosing and dispensing mechanism.

WO 98/26828 and WO 03/051439 disclose several delivery devices for use with medicament containers that have openings through which medicament is dispensed within the delivery device. The delivery devices all comprise a mouthpiece in fluid communication with a chamber, in which the medicament container is located. The chamber itself is in direct fluid communication with the exterior of the device via air inlet means. In use, air is drawn into the chamber through the air inlet means, which generates motion of the medicament container in the chamber, causing medicament to be dispensed from the container and entrained within the air flow, such that the airflow with entrained medicament is inhaled through the mouthpiece. The disclosed delivery devices include single-use devices pre-loaded with a medicament container and multi-use devices in which medicament containers may be inserted into the chamber before or between uses. In addition, WO 03/051439 discloses a holder for the medicament container comprising a deformable cup in the wall of the chamber, from which a medicament container is expelled by applying pressure to the exterior of the cup.

The delivery devices disclosed in WO 98/26828 and WO 03/051439 represent a considerable advance over the prior art, but may nonetheless be further improved.

SUMMARY

There has now been devised an improved delivery device that overcomes or substantially mitigates the above mentioned and/or other disadvantages associated with the prior art.

According to a first aspect of the invention, there is provided a delivery device comprising a container containing a dose of a powder, a chamber adapted to receive the container, at least one gas inlet by which gas may enter the chamber, and at least one gas outlet by which gas and entrained powder may exit the chamber for inhalation, the delivery device having a pre-use configuration in which the container is accommodated, at least partially, within a storage enclosure in a wall of the chamber, the delivery device having a deployment member adapted to put the delivery device in an operative configuration by displacing the container from the storage enclosure into the chamber, such that the container is movable within the chamber, in use, the deployment member being adapted to at least partially occupy the storage enclosure in the operative configuration.

The delivery device according to this invention is advantageous principally because the deployment member is adapted to at least partially occupy the storage enclosure in the operative configuration, and hence overcome or substantially mitigate disadvantages associated with the presence of a vacant storage enclosure in a wall of the chamber. In particular, the presence of a vacant storage enclosure in a wall of the chamber may reduce the efficiency of gas flow within the chamber, with regard to driving movement of the container, in use. A vacant storage enclosure in a wall of the chamber may also provide additional surface area upon which the powdered formulation may be deposited, in use. Furthermore, the vacant storage enclosure may interfere with movement of the container within the chamber, in use, which may affect effective dispensing of the powder.

The container preferably includes one or more exit orifices, which enable emission of powder from the container, in the operative configuration. The storage enclosure is preferably adapted to retain the container at least partially therein, in the pre-use configuration, such that the one or more exit orifices are sealed. In particular, the exit orifices are preferably sealed to a sufficient extent that powder is retained within the container in the pre-use configuration.

The container is preferably retained within the storage enclosure by means of an interference fit between the container, and an interior surface of the storage enclosure. However, alternative, or indeed additional, retaining formations may be provided. In preferred embodiments, the container is retained in a manner that prevents the container being inadvertently dislodged from the storage enclosure during normal handling, in the pre-use configuration. In presently preferred embodiments, the interference fit between the container, and an interior surface of the storage enclosure, acts to seal the one or more exit orifices of the container.

The delivery device is preferably adapted to prevent the ingress of moisture into the container. Where the delivery device is a single-use device, this may be achieved by supplying the delivery device in packaging formed of a material with a low moisture vapour transmission rate, such as a sealed foil packet, which is opened by the patient before use. In this case, there is no need for the container to be substantially impermeable to moisture.

Alternatively, where the delivery device is a multi-use device and therefore cannot be sealed in moisture impermeable packaging before each use, the delivery device itself is preferably arranged to prevent unacceptable ingress of moisture into the container, for example to prevent spoiling of the powder within the container before use. In particular, where the container includes one or more exit orifices, and these one or more exit orifices are sealed until the device is used, which may be achieved by the fit between the container and an interior surface of the storage enclosure being sufficient to prevent the ingress of an unacceptable amount of moisture into the container. The moisture resistance of the container may also be improved by spray-coating the surface of the container with a moisture resistant material, which is particularly preferable where the material of the container has a relatively high MVTR.

The container and/or the interior surface of the storage enclosure are preferably relatively compliant to improve the seal between these surfaces. In addition, the container and recess are preferably formed of materials with a low moisture vapour transmission rate. The desired compliance of the container and/or the interior of the storage enclosure may be achieved by these components having resiliently movable portions, eg formed by a hinged arrangement.

In particular, the compliance of the interior surface of the storage enclosure that engages the container may be increased by the presence of a groove that circumscribes the storage enclosure opening, and defines an inner wall located between the groove and the storage enclosure opening, which is resiliently deformable outwardly to accommodate the container.

Alternatively, the container and/or the storage enclosure may include a compliant member formed of a less rigid material than the remainder of the component, such as an elastomeric material. In particular, the portion of the interior surface of the storage enclosure that engages the container may be provided with a compliant member formed of silicone or thermoplastic elastomer (TPE). The compliant member may be formed in a two-step injection moulding process, in which the components forming the storage enclosure are moulded in the first step and the compliant member is moulded onto one or more of those components in the second step. Alternatively, the compliant member may be bonded to the interior surface of the storage enclosure by other means, such as with an adhesive or by heat welding. The compliant member could instead, or in addition, be provided on the corresponding portion of the exterior surface of the container.

The compliant member may compensate for dimensional variations in components commonly encountered in high volume manufacturing. In particular, relatively large dimensional variations in the components may affect the interference fit between the container and an interior surface of the storage enclosure, either allowing the container to become dislodged from the storage enclosure or conversely resulting in the force required to overcome the interference fit being increased to undesirable levels. Increasing the compliance of the container and/or the interior of the storage enclosure may compensate for greater dimensional variation in the components and ensure that an effective fit is maintained. In particular, where a particularly high level of compliance is required, the storage enclosure may comprise a compliant member that includes a particularly compliant formation, such as a lip seal.

The deployment member is preferably movably mounted relative to the chamber, such that the deployment member displaces the container from the storage enclosure on movement from a pre-use position to an operative position. The deployment member preferably contacts the container, and urges the container from the storage enclosure, on movement of the deployment member from the pre-use position to the operative position. The deployment member may be moved manually by the user, or may be moved by a deployment mechanism that is activated by the user.

At least an end portion of the deployment member is preferably movable within a side wall of the storage enclosure, which may have the form of a sleeve, such that movement of the deployment member from a pre-use position to an operative position displaces the container from the storage enclosure. In presently preferred embodiments, the deployment member defines a wall of the storage enclosure in the pre-use configuration. In particular, the deployment member preferably defines an end wall of the storage enclosure.

The deployment member may be movably mounted relative to the chamber in any suitable manner. In presently preferred embodiments, the deployment member is slidably mounted relative to the chamber, for example within a sleeve that defines a side wall of the storage enclosure. However, the deployment member could be moved by operation of a threaded connection, for example within a sleeve that defines a side wall of the storage enclosure.

The deployment member is preferably retained in a pre-use position by retaining formations, which are preferably adapted to maintain the deployment member in the pre-use position during normal handling. These retaining formations are preferably adapted to be overcome by a user purposively moving the deployment member into an operative position. The retaining formations preferably have the form of a cooperating projection and recess, which are engaged in the pre-use configuration with a snap fit. The retaining formations may be adapted to enable movement of the deployment member into an operative position, but prevent other movement, such as removal of the deployment member from the delivery device, without damaging the delivery device.

The deployment member is preferably movable towards a mouth of the storage enclosure, through which the container is released into the chamber. The storage enclosure preferably reduces in volume as the deployment member is moved from a pre-use position to an operative position, until at least the container is displaced into the chamber, and hence the deployment member at least partially occupies the storage enclosure.

In the operative configuration, the storage enclosure is preferably reduced sufficiently in volume that the gas flow within the chamber, in use, is not adversely affected by the presence of the storage enclosure. The storage enclosure is preferably reduced in volume by at least 30%, more preferably by at least 50%, and most preferably by at least 70%. In presently preferred embodiments, however, the storage enclosure is preferably substantially removed from the wall of the chamber by means of the deployment member being accommodated within a mouth of the storage enclosure, preferably such that the deployment member provides a surface of the chamber that is substantially flush with the adjacent surfaces of the wall of the chamber.

The deployment member is preferably retained in its operative position, during use. In particular, the deployment member may be retained by means of the engagement between the deployment member and the wall defining the storage enclosure, for example by an interference fit or a threaded connection. However, in addition, the deployment member is preferably adapted to be retained in its operative position either permanently, for example in a single-use device, or until actuation of an indexing mechanism of the delivery device.

The deployment member is preferably retained in the operative position by retaining formations. In presently preferred embodiments, the deployment member is retained by a wall defining the storage enclosure, in the operative position, by cooperating retaining formations. The retaining formations preferably have the form of a cooperating projection and recess, which are engaged in the operative configuration with a snap fit. Where the delivery device is a single-use, disposable device, the retaining formations may be adapted to prevent further movement of the deployment member, without damaging the delivery device.

In a presently preferred embodiment, the deployment member defines at least part of an inhalation passageway of the delivery device, through which gas and entrained powder exit the device. The deployment member may comprise a wall that forms part of the wall of the chamber, in the operative configuration, and in which one or more of the gas outlets are formed, such that gas and entrained powder flow through that wall, in use. Where the chamber has the shape of a drum, the deployment member preferably comprises a wall that forms part of an end wall of the chamber. The deployment member may define an inhalation passageway that extends from the wall in which the one or more of the gas outlets are formed. The deployment member may also define the opening through which gas and entrained powder are withdrawn from the device in use, and may comprise as a mouthpiece, nosepiece or a means for engaging the device with a breathing circuit or the like. This arrangement is particularly advantageous in that it reduces the number of components required to provide the delivery device.

In this embodiment, the deployment member is preferably moveably mounted within a sleeve that extends from an exterior surface of a wall of the chamber. A seal is preferably formed between the exterior surface of the deployment member and the interior surface of the sleeve, such that gas and entrained powder does not leak between these surfaces. This seal may take the form of any suitable sealing arrangement, such as integral sealing ridges on one of the surfaces, such as radiused sealing ridges.

Where the deployment member is moveably mounted within a sleeve, the deployment member may be received within the sleeve to a greater extent in the operative position, relative to the pre-use position. The deployment member may therefore include indications that are visible in the pre-use configuration, and hidden in the operative configuration, for example by the sleeve, in order to indicate the status of the delivery device. Other embodiments may include different indications of the status of the delivery device.

The storage chamber and the container may form an integral part of the delivery device. In particular, the delivery device may be a single-use, disposable delivery device, or may be a multi-dose delivery device, in which one or more containers are retained within the delivery device until use. Alternatively, the storage enclosure and the container may form a package, which is engageable with the delivery device prior to use. This arrangement enables packages to be supplied to a user, for use with a reusable delivery device. In this arrangement, the delivery device may not retain any containers prior to use.

The at least one gas inlet of the device is preferably arranged such that gas enters the chamber substantially tangentially, for example so as to generate a turbulent rotating body of gas in the chamber, which facilitates the orbital motion of the container within the chamber. There are preferably provided a plurality of gas inlets, most preferably opening into the chamber at substantially equiangularly spaced positions. The gas inlets may include narrowed portions to act as venturi and thereby increase the speed of the gas flow into the chamber.

It is particularly preferred that a part of the wall of the chamber into which the gas inlets open should be continuous and unbroken in order to inhibit any tendency for the movement of the container to be affected by the edges of the gas inlet openings. In preferred embodiments, the gas inlets open into the circumferential wall of the chamber, but have a depth which is less than the height of that wall so at least part of the wall, such as the lower and/or upper part of that wall, forms an uninterrupted annular surface.

The at least one gas outlet may take any suitable form provided that, in use, it retains the container within the chamber whilst permitting gas and entrained powder to pass out of the chamber. In preferred embodiments, the at least one gas outlet comprises a mesh or grid formed in part of the chamber wall. Most preferably, the mesh or grid lies in a plane which is parallel to the plane in which container moves. For example, where the chamber is substantially drum shaped, the mesh or grid may be formed in the end walls of the chamber.

In particularly preferred embodiments, the grid or mesh should extend over only part of the lower wall of the chamber, most preferably the central part of the upper or lower wall. The radial outer part of the upper or lower wall is therefore preferably solid, which facilitates the generation of a turbulent rotating body of gas around the circumferential edge of the chamber and increases the residency time of the gas and entrained powder in the chamber, which enhances milling of the powder between the container and chamber wall, improving powder deagglomeration. Most preferably, the solid outer part of the upper or lower wall forms an annulus having a width corresponding to at least 15% of the radius of that wall, more preferably at least 20%.

Gas and entrained powder may exit the device by any suitable means but preferably exit the device via a suitable opening. The device is most commonly intended to administer powder directly to a patient by oral inhalation, in which case the opening may comprise a mouthpiece for engagement with the mouth of a patient. However, administration may be by any other suitable means and, in particular, may be by nasal inhalation, in which case the opening may comprise a nosepiece for engagement with the nose of a patient. Administration may also be through a breathing circuit or the like, in which case the opening may comprise a means for connecting the device with such a circuit. The opening is preferably formed at the open end of a passageway or conduit which communicates with the chamber via the at least one gas outlet. A particularly preferred arrangement is provided if the passageway or conduit is oriented parallel to the axis of rotation of the container in the chamber, but in other embodiments the passageway or conduit may be oriented substantially orthogonally to that axis.

The device may be manufactured from materials conventionally utilised in devices for orally administering powders. For example, the device may be manufactured from a plastics material such as acrylonitrile butadiene styrene (ABS), polycarbonate, a polyolefin such as polypropylene or polyethylene, or any other suitable plastics material. Other suitable materials include metals such as aluminium and stainless steel. Combinations of different materials may be used, with each component being formed from the most suitable material or materials.

Embodiments of the device may be configured for repeated use. In such a case, means are provided for introducing a container into the chamber before each use and removing the container after use. For example, the chamber may be provided with a removable cover, which may have a snap fit or hinged connection to the rest of the device such that it can be opened to insert a container into the chamber, closed during use of the device and then opened again for removal of the spent container. However, in preferred embodiments, the device is for single use, in which case the device may be supplied pre-loaded with a container.

Whilst the delivery device is intended primarily for use in which inhalation by the patient leads to the necessary motion of the container and emission of the powder from the container, a source of pressurised air or other gas may be used to produce or assist in bringing about motion of the container. This arrangement is particularly preferable where the mass of the container is too great to be effectively driven by the gas flow generated by a patient. For example, the delivery device may include a source of compressed gas, which facilitates dispensing of the powered formulation to the patient, via a spacer chamber. The delivery device may also be intended for engagement with a breathing circuit or the like, in which case the motion of the container may be brought about by the gas flow through the breathing circuit.

The container preferably has a substantially circular cross-section but may have any overall shape that allows the container to undergo motion suitable to cause powder to be emitted from the one or more orifices. In order to reduce the amount of material required to construct the container, and hence reduce the weight of the container, for a given volume of the container, a sphere would be the preferred choice. However, in preferred embodiments, the container is generally cylindrical, and preferably has a diameter greater than its height. This arrangement facilitates manufacture and charging of the container with the powder. In addition, this arrangement may be adapted to maintain the container in an upright orientation relative to the chamber.

The upper and lower end walls of the cylinder may be substantially flat, or one or both end walls may be either convex or concave. However, the upper and lower end walls of the container are preferably convex to reduce the contact area between the container and the chamber, thereby reducing friction between the components as the container undergoes motion. In addition, it is particularly preferable that the surface of the container that is adjacent to the mesh or grid is convex to prevent the container lying flat on the grid or mesh, which could lead to the container being immobilised on the grid or mesh by suction.

In other embodiments, the container may be substantially spherical in order to reduce the amount of material required to construct the container, and hence reduce the weight of the container.

The clearance between the upper and lower end walls of the container and the chamber is preferably relatively low to improve the stability of the container as it undergoes motion. In addition, it is preferred that a relatively small proportion of the free volume of the container is located between the end walls of the container and the chamber as gas flow in these regions is less effective in bringing about motion of the container. In particular, it is preferred that the minimum clearance between the end walls of the container and the chamber is less than 25% of the height of the chamber, more preferably less than 15%, yet more preferably less than 10% and most preferably less than 5%, less than 3% or less than 1% of the height of the chamber.

The container may have any suitable construction, but is preferably formed of a number of cooperating components. Most preferably, the container is formed from two cooperating components fastened together by any suitable means, such as by snap fit, screw fit, bayonet or ultrasonic welding. The container may also be formed as a single component with the two cooperating components being connected by a hinge. The container preferably comprises a cup component and a lid component, where the lid component is engageable with the cup component, and the cup component and a lid component define the internal volume of the container. In a preferred embodiment, the cup component is of generally cylindrical construction, open at one end, and a lid component fastens over the open end of the cup, thereby completing the cylindrical container. The preferred fastening means in this embodiment is a snap fit, either circumferentially or by means of a central pin.

In the cup and lid embodiment, the cup component is preferably adapted to receive the dose of powder during manufacture, prior to engagement of the lid component with the cup component to form the assembled container. The cup component may be formed with a greater internal volume than is occupied by the dose of powder, in order to reduce the risk of powder being spilt during filling. In this arrangement, at least, the cup component preferably has a greater internal volume than the lid component.

The container may have only a single compartment in which powder is contained. The container may also comprise two or more compartments, particularly where two or more different powders are to be administered as each powder may be contained in a separate compartment, although the same powder may be contained in each compartment. Where multiple compartments are present, each compartment preferably has at least one exit orifice.

The one or more exit orifices in the container may be formed in one or both of the components or may alternatively be defined between the two components. The at least one exit orifice may be preformed in the container, in that the at least one exit orifice is created in the container prior to its introduction into the delivery device. Most preferably, however, the at least one exit orifice is integrally formed with the container, in that the at least one exit orifice is created in one or more components of the container during their manufacture. For example, the at least one exit orifice may be formed during the moulding of one or more components of the container. In this arrangement, the at least one exit orifice is preferably closed by a closure member before the container is brought into an operative configuration.

Most preferably, a plurality of exit orifices is provided, for example two exit orifices. The exit orifices may advantageously be disposed around the circumference of the cylindrical container, preferably at substantially equiangularly spaced locations.

The container may be formed from any suitable material or combination of materials with the most preferred materials being relatively lightweight, to reduce the gas flow required to move the container, and sufficiently resilient to withstand relatively high rotational speeds of the container within the chamber. The container is preferably moulded from plastic materials such as acrylonitrile butadiene styrene (ABS), polycarbonate, a polyolefin such as polypropylene or polyethylene, and others.

The container may include a non-solid component, such as a component formed of a sheet material such as metal foil or plastic film. Such components may be fastened to other components of the container by any suitable means, such as with adhesives, heat sealing or ultrasonic welding. In one particular embodiment of a container comprising a component formed of a sheet material, the container comprises a solid cup moulded from plastics material and a lid formed of a sheet material which seals the open end of the cup component.

The preferred materials for forming the container may be substantially impermeable to moisture, in order to protect the powder from being spoiled by moisture when the one or more openings are sealed. This may reduce or eliminate the need for secondary packaging, thus reducing the complexity of the manufacturing operation and also simplifying use of the device. In general, materials with lower moisture permeability are preferred as a lower thickness is required to provide an effective moisture barrier, leading to a reduction in weight and hence to a reduction in the gas flow necessary to cause the container to move. However, the container or device may be provided in a moisture proof packet, in which case there is no need for the container to be substantially impermeable to moisture.

The diameters of the container and the chamber are preferably chosen to provide sufficient clearance between the container and the chamber to allow sufficient motion of the container to bring about the desired level of powder emission from the at least one exit orifice. The minimum effective clearance depends on the desired powder emission rate and flow properties of the powder, but the diameter of the container must be less than the diameter of the chamber and in general is no greater than 99% or no greater than 95% of the diameter of the chamber.

It is believed that the diameter of the container being at least 50%, and more preferably at least 60%, of the diameter of the chamber promotes epicyclic motion of the container. Furthermore, arrangements in which the diameter of the container is between 70% and 85%, or more particularly between 75% and 80%, of the diameter of the chamber have been found to be particularly effective in promoting epicyclic motion of the container. In one particularly preferred embodiment, which has been found to promote epicyclic motion, the container has a diameter of 18 mm and the chamber has a diameter of between 22 mm and 24 mm, most preferably 23 mm.

It has been found that this device allows amounts of powder of greater than 40 mg to be effectively administered from a single container by repeated inhalations, without the need to manipulate the delivery device between inhalations, for example by reloading or reactuation of the delivery device. In particular, the delivery device of this invention may include a container containing a dose of at least 60 mg, at least 80 mg, at least 100 mg, at least 200 mg, at least 300 mg, at least 400 mg, at least 600 mg or at least 800 mg of powder.

The delivery device of this invention may be used for the delivery of any powder that is suitable for oral delivery. In particular, the device may be used to administer powdered medicaments, such as antimicrobial agents including antibiotics and antifungals for the treatment of infections, and bronchodilators including salbutamol or formoterol for the treatment of asthma or chronic obstructive pulmonary disorder. The device is also suitable for administering other substances that are in the powder form, such as radioactive markers, vaccines, proteins such as insulin for the treatment of diabetes, or antibodies. The device is particularly suitable for administering osmotic agents such as mannitol for the treatment of cystic fibrosis.

The device may be used to administer powders consisting of one or more powdered medicaments only or comprising powdered medicament and a powdered carrier. Carriers are generally added to powdered medicament formulations to improve their handling characteristics or act as a bulking agent and generally do not have a medical effect. Powder formulations administered by the device may comprise any desired ratio of medicament and carrier, such as 30%, 20% or 10% w/w of powdered medicament. However, powder formulations that include a carrier typically comprise less than 5%, less than 4%, less than 3%, less than 2%, less than 1%, less than 0.5% or less than 0.2% w/w of powdered medicament, with the remainder of the formulation being made up of carrier.

The device may be used to administer powders that are present in a range of particle sizes. Powders that are intended to reach the lung are preferably present in respirable particle size, ie particle sizes that tend not to be deposited in the mouth and throat and pass into the lung. Reparable particle size is generally considered to be below 10 µm, although particles sizes below 6 µm and particularly below 5 µm are particularly effective at reaching the lung. However, particles below 1 µm in size may not be deposited effectively in the lung and be exhaled. Alternatively, particles may be present in non-respirable particle size, which tend not to reach the lung and are instead deposited in the mouth and throat. Non-respirable particle size is generally considered to be greater than 10 µm, more usually greater than 40 µm and generally around 50 µm.

The powders administered by the delivery device of this invention may comprise a range of particle sizes, for example comprising a combination of particles of respirable and non-respirable particle sizes. For example, the device may be used to administer powder comprising a medicament that is substantially present in respirable particle size and a carrier that is substantially present in non-respirable particle size, although carrier may also be present in respirable particles size. The powder is preferably entirely of respirable particle size, particularly where larger doses are administered, in order to avoid inducing a cough response because of powder deposition in the throat.

In presently preferred embodiments, the delivery device includes a container containing a dose of greater than 40 mg or at least 60 mg, at least 80 mg, at least 100 mg, at least 200 mg, at least 300 mg, at least 400 mg, at least 600 mg or at least 800 mg of respirable particles.

The container is preferably not completely filled with a powder, such that the powder may move within the container during use. In particular, the container preferably includes a headspace that allows the powder to flow and tumble within the container, facilitating emission of the powder from the at least one exit orifice. For example, headspace preferably accounts for at least 5% of the internal volume of the container. In presently preferred embodiments, however, the headspace accounts for between 20% and 40% of the internal volume of the container. However, effective levels of powder emission may still be achieved where no headspace is present, particularly where the powder is uncompacted within the container.

The container is preferably adapted to restrict the emission of the powder from the container, such that powder is emitted from the container steadily as it is undergoing motion. This is advantageous over conventional delivery devices, in which the entire powder dose is typically dispensed as soon as the patient starts to inhale, principally because steady powder emission is less likely to induce a cough response. It may therefore be possible to deliver a greater quantity of powder in each inhalation relative to conventional delivery devices.

The restriction of powder emission from the container may be achieved by the one or more exit orifices being of a relatively small size. The specific size of the one or more exit orifices may be selected depending on the desired powder emission rate and the flow properties of the particular powder. Where the motion of the container is brought about by the gas flow generated by the inhalation of a patient, the emission rate is preferably such that powder is steadily emitted from the container, eg at a substantially uniform rate, during the majority of the inhalation, and most preferably during substantially the entire inhalation. The one or more exit orifices preferably have a combined cross-sectional area of less than 1 $mm^2$, more preferably less than 0.5 $mm^2$, and most preferably less than 0.3 $mm^2$.

The restriction of powder emission from the container may be achieved by other means, such as restricting the motion of the powder within the container with one or more formations on the interior of the container. Therefore, according to a further aspect of the invention, there is provided a container having at least one exit orifice for dispensing powder, the container being adapted to be received within a chamber of a delivery device, the device further comprising at least one gas inlet by which gas may enter the chamber and at least one gas outlet by which gas and entrained powder may exit the chamber, wherein the container comprises one or more internal formations for restricting the motion of powder within the container.

These one or more formations may sufficiently restrict powder emission from the container alone such that there is no need for the exit orifices to be of a relatively small size. The one or more formations may take any suitable form but are preferably projections projecting from the internal wall of the container into the interior of the container, such as walls or baffles. The one or more formations preferably partially divide the internal volume of the container into a number of sub-chambers with the passage of powder between each sub-chamber being permitted through gaps or openings in or between the one or more formations. In particularly preferred embodiments, the sub-chamber or chambers in which the one or more exit orifices are located are separate from the sub-chamber or chambers that initially contain the majority of the powder.

In addition, the container may be provided with one or more formations on its exterior surface for increasing gas flow resistance. Therefore, according to yet a further aspect of the invention, there is provided a container having at least one exit orifice for dispensing powder, the container being adapted to be received within a chamber of a delivery device, the device further comprising at least one gas inlet by which gas may enter the chamber and at least one gas outlet by which gas and entrained powder may exit the chamber, wherein the container comprises one or more external formations for increasing gas flow coupling.

Increased coupling between the gas flow and the container may improve the efficiency of the device and/or influence the motion of the container by increasing the friction between the gas flow and the container. These one or more formations are preferably located on the circumferential wall of the container, which is where the gas flow may apply the greatest rotational force to the container. The formations preferably do not project substantially beyond the circumferential surface of the container such that they do not substantially interfere with the motion of the container. The one or more formations preferably comprise a textured surface and most preferably a series or grooves and/or ridges. In one particularly preferred embodiment, the circumferential wall of the container is provided with a series of grooves and ridges that are aligned perpendicularly to the direction of the gas flow.

BRIEF DESCRIPTION OF THE DRAWINGS

A preferred embodiment of the invention will now be described in greater detail, by way of illustration only, with reference to the accompanying drawings, in which.

DETAILED DESCRIPTION OF THE EMBODIMENTS

Figure 1:
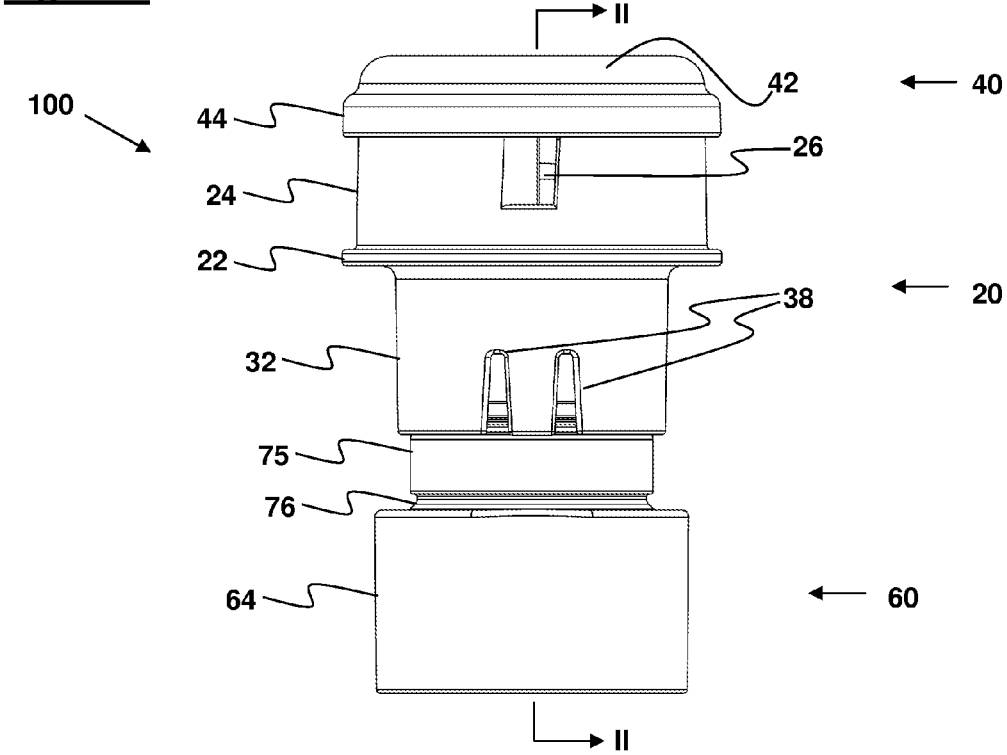
FIG. 1 is a side view of a delivery device according to the invention.

FIGS. 1 to 6 show a first embodiment of a delivery device according to the present invention, which is generally designated 100. The delivery device 100 comprises body 20 and mouthpiece 60 components formed in a high density polyethylene, and a cap 40 component formed in a polycarbonate, each formed by injection moulding. The delivery device 100 also includes a container that is generally designated 80 in the drawings.

The delivery device 100 is a single-use, disposable device, which is supplied in sealed, foil packaging, which prevents the ingress of moisture. The delivery device 100 is supplied with the container 80 loaded with a dose of approximately 400 mg of powder. In particular, the specific powder for this embodiment of the invention is mannitol, formulated as a dry respirable powder. For clarity, the powder has been omitted from the drawings. The delivery device 100 is adapted to deliver the dose of powder contained within the container 80 in a single use, through several inhalations, as discussed in more detail below. The delivery device 100 is adapted to then be discarded.

Figure 2:
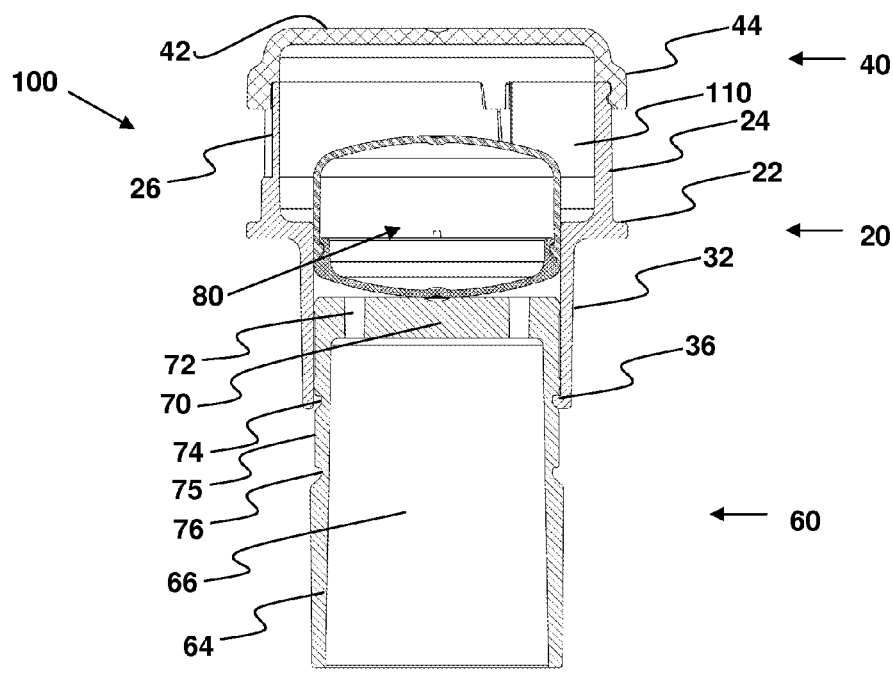
FIG. 2 is a cross-sectional view of the delivery device, along the line II-II in FIG. 1.
Figure 3:
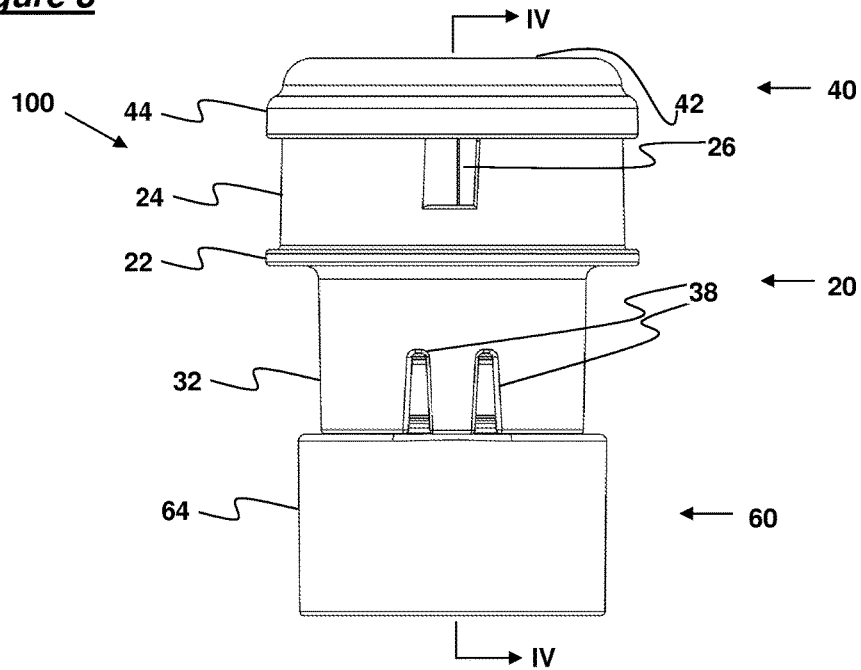
FIG. 3 is a side view of the delivery device in its operative configuration.
Figure 4:
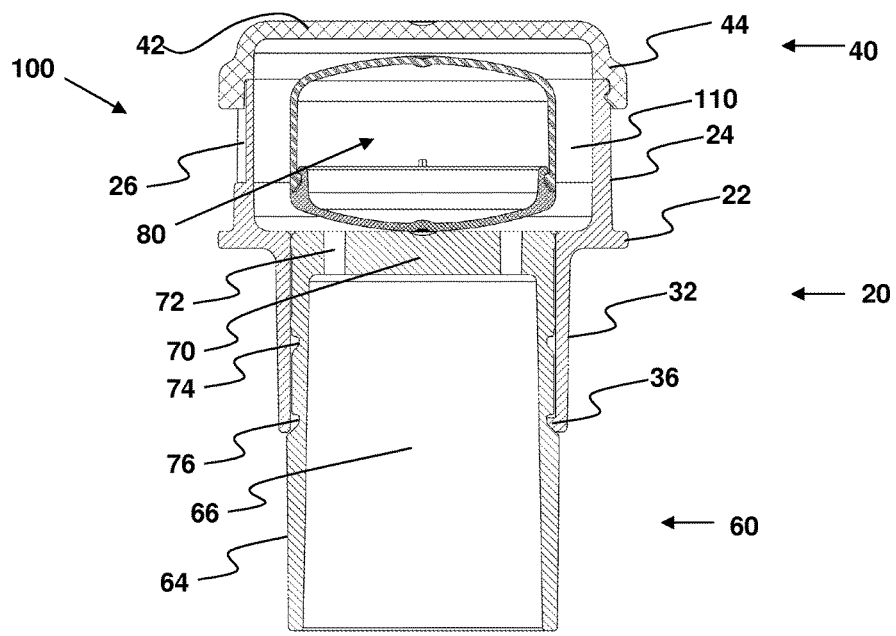
FIG. 4 is a cross-sectional view of the delivery device in its operative configuration, along the line IV-IV in FIG. 3.
Figure 5:
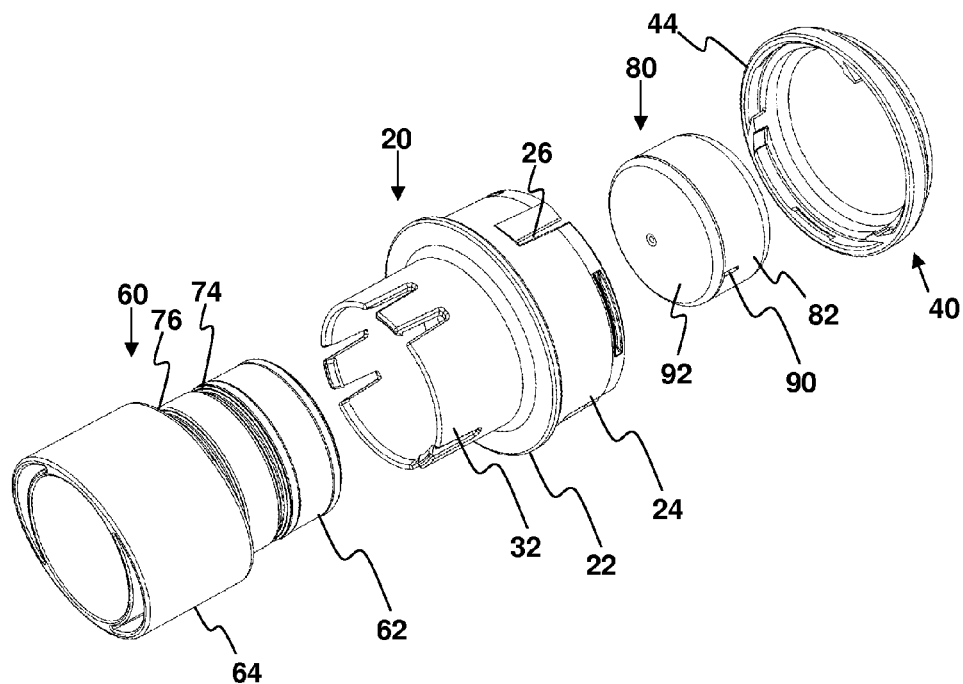
FIG. 5 is a first exploded view of the delivery device.
Figure 6:
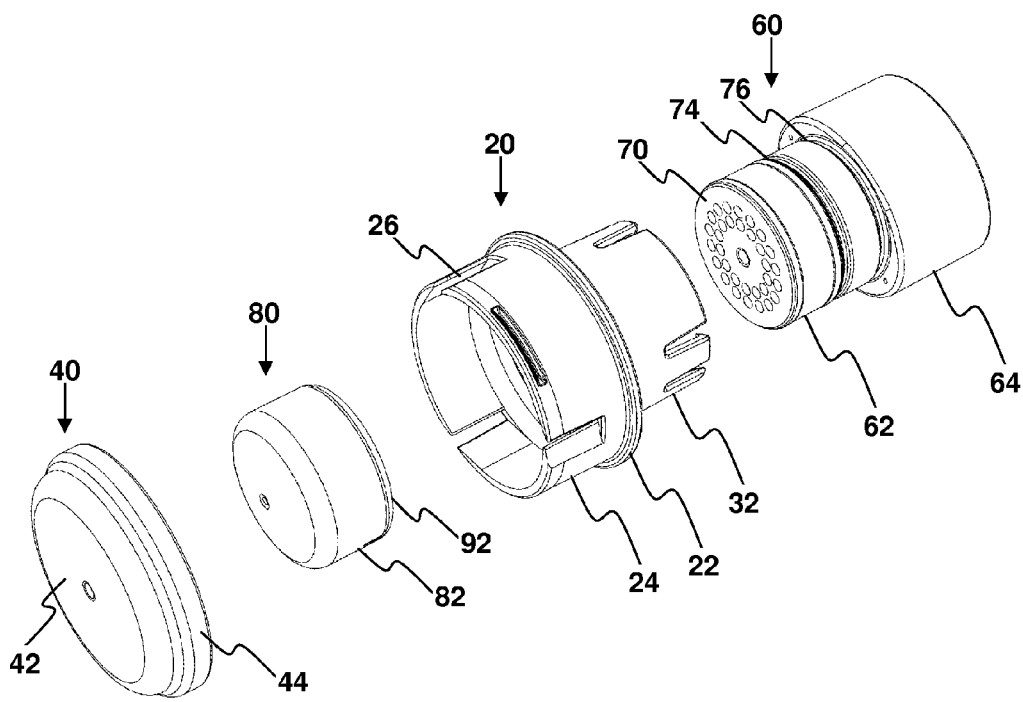
FIG. 6 is a second exploded view of the delivery device.

FIGS. 1 and 2 show the delivery device 100 in its pre-use configuration, with the container 80 in a storage position. FIGS. 3 and 4 show the delivery device 100 in its operative configuration, with the container 80 deployed into a cylindrical chamber 110 defined by a combination of the body 20, cap 40 and mouthpiece 60 components. In particular, the chamber 110 comprises an outer end wall defined by the cap 40, an inner end wall defined by the body 20 and the mouthpiece 60, and a cylindrical side wall defined by the body 20 and the cap 40. Each of the components 20, 40, 60 of the delivery device 100, and their relative arrangements, are described in more detail below.

Figure 7:
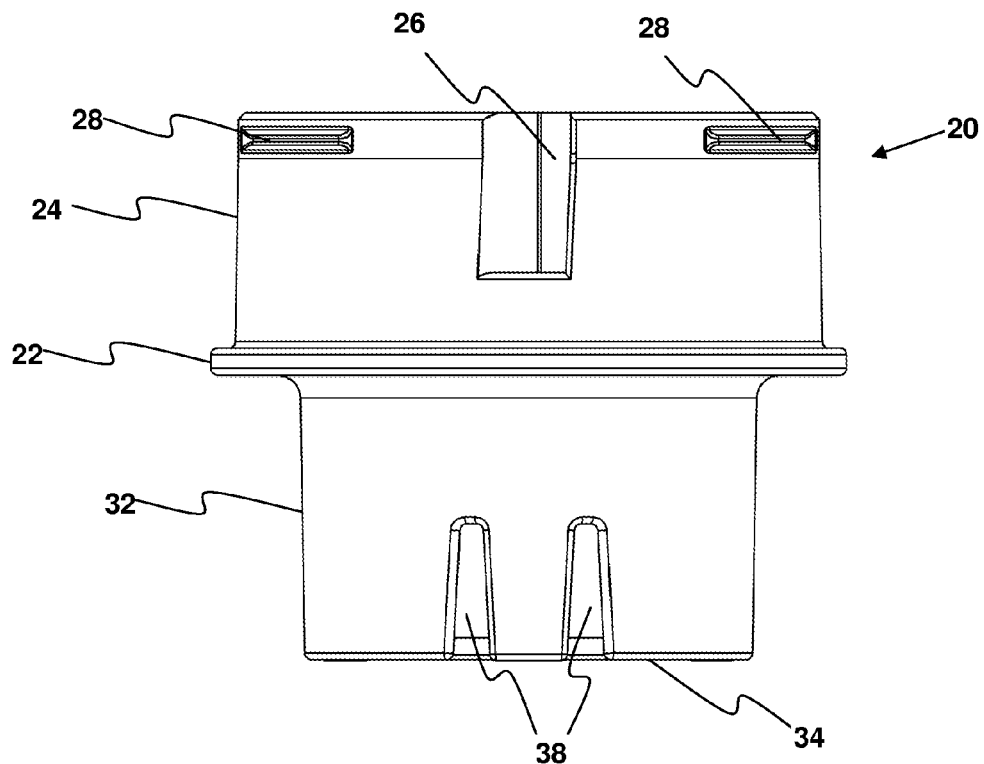
FIG. 7 is a side view of a body, which forms part of the delivery device.
Figure 8:
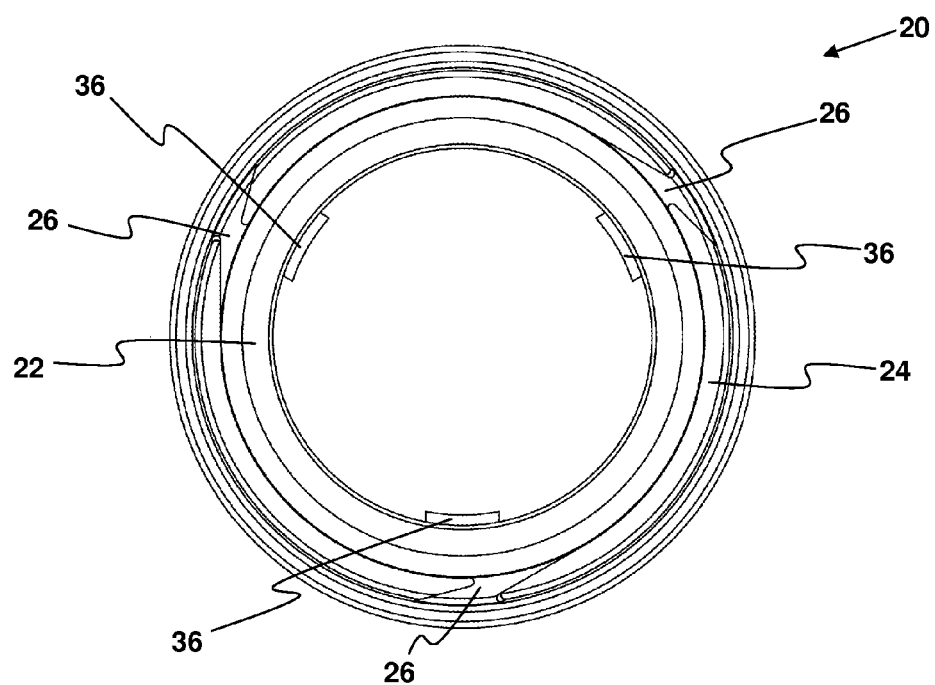
FIG. 8 is a plan view of the body.
Figure 9:
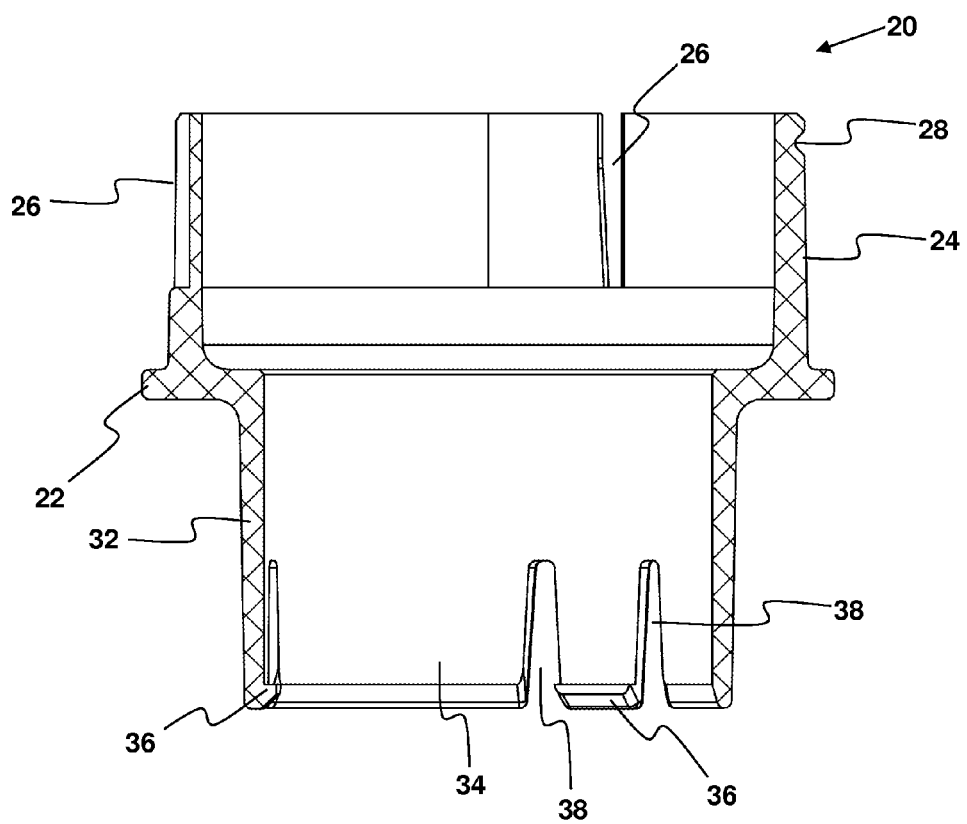
FIG. 9 is a cross-sectional view of the body.

The body 20 is shown in isolation, and in greater detail, in FIGS. 7 to 9. The body 20 comprises a cylindrical wall 24 and a cylindrical sleeve 32 of reduced diameter, which are arranged co-axially and extend from each side of an annular support 22.

The cylindrical wall 24 of the body 20 forms the majority of the side wall of the cylindrical chamber 110, in the delivery device 100, and includes three evenly spaced gas inlet slots 26 through which gas may enter the chamber 110, in use. Each of the gas inlet slots 26 extend from the end of the cylindrical wall 24 remote from the annular support 22, to a position approximately three quarters of the way towards the annular support 22. The gas inlet slots 26 each have the form of a passageway through the cylindrical wall 24, which extends in a generally tangential direction relative to the chamber 110. In particular, each gas inlet slot 26 is arranged to introduce a flow of gas along the interior surface of the cylindrical wall 24, and hence the chamber 110, such that gas that flows into the chamber from the three gas inlet slots 26, in use, are directed around the circumference of the chamber 110, thereby generating a turbulent rotating body of gas within the chamber 110.

The cylindrical sleeve 32 of the body 20 extends from the annular support 22 in the opposite direction to the cylindrical wall 24. The sleeve 32 has an open outer end 34, the rim of which has three evenly-spaced, inwardly-facing projections 36. Notches 38 are located in the rim of the sleeve 32 on both sides of each projection 36, which allow the regions of the sleeve 32 in which the projections 36 are located to bend more freely. In particular, these regions of the sleeve 32 have the form of elastically deformable arms, with the inwardly-facing projections 36 at the distal ends of those arms.

Figure 10:
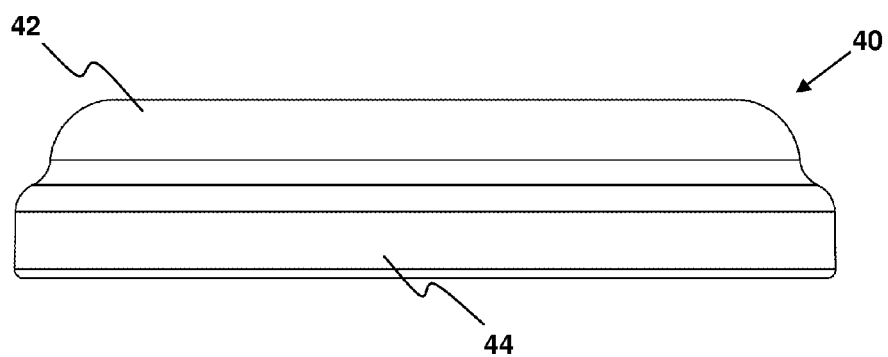
FIG. 10 is a side view of a cap, which forms part of the delivery device.
Figure 11:
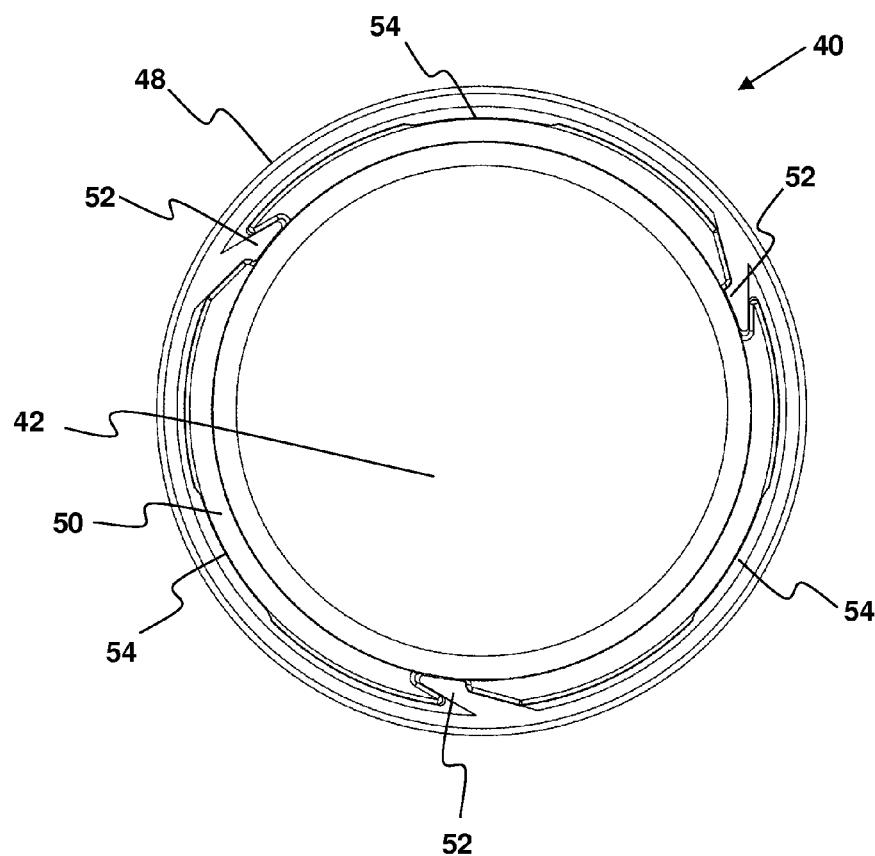
FIG. 11 is an underside view of the cap.
Figure 12:
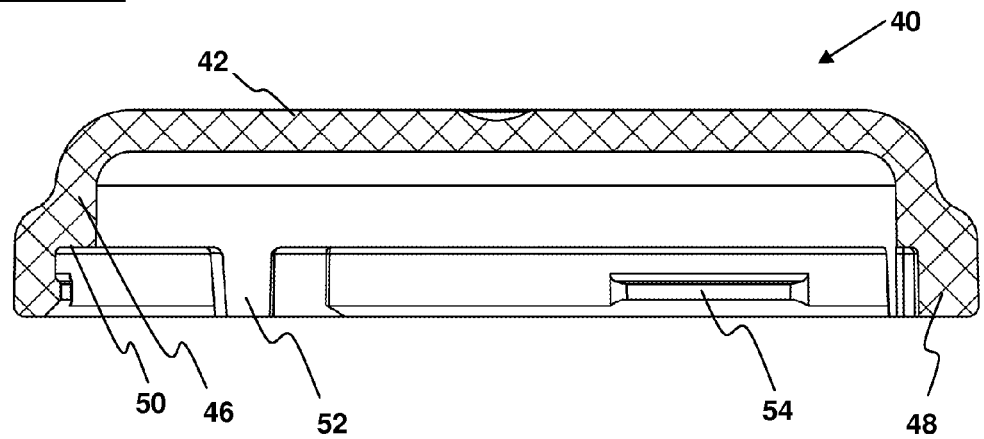
FIG. 12 is a cross-sectional view of the cap.

The cap 40 is shown in isolation, and in greater detail, in FIGS. 10 to 12. The cap 40 comprises a circular end wall 42, which forms the outer end wall of the cylindrical chamber 110. The end wall 42 is substantially transparent to allow a user to view the interior of the chamber 110.

The cap 40 also has a peripheral skirt 44, which extends generally perpendicularly from the end wall 42. The skirt 44 is arranged to connect the cap 40 to the end of the cylindrical wall 24 of the body 20, such that the body 20 and the cap 40 define the side wall and outer end wall of the chamber 110.

The skirt 44 has a proximal portion 46 and a distal portion 48. The proximal portion 46 extends generally perpendicularly from the periphery of the end wall 42, and defines an end portion of the side wall of the chamber 110. In particular, an internal shoulder 50 is formed between the proximal and distal portions 46, 48 of the skirt 44, which has a downwardly facing surface substantially parallel to the plane of the end wall 42, and which abuts the end of the cylindrical wall 24 of the body 20. The internal diameter of the proximal portion 46 is substantially equal to that of the cylindrical wall 24 of the body 20, such that the chamber 110 has a uniform diameter.

The distal portion 48 has a slightly increased diameter relative to the proximal portion 46, and extends from the end of the proximal portion 46. The inwardly facing surface of the distal portion 48 has a diameter that is substantially equal to the diameter of the external surface of the cylindrical wall 24 of the body 20, such that the cylindrical wall 24 of the body 20 is received within the distal portion 48 of the skirt 44, with the upper surface of the cylindrical wall 24 abutting the interior shoulder 50. The cap 40 is locked in place by a number of projections 54 on the inwardly facing surface of the distal portion 48 of the skirt 44, which engage corresponding recesses 28 located at the upper end of the outer surface of the cylindrical wall 24 with a snap fit.

The internal surface of the skirt 44 further includes three tangential projections 52 that are received within the upper ends of the gas inlet slots 26 in the cylindrical wall 24 of the body 20. The tangential projections 52 occupy end portions of the slots 26, with a close fit, restricting the gas inlets defined by the slots 26 to those portions of the gas inlet slots 26 that are free of the projections 52 of the cap 40, arranged in an intermediate region of the circumferential wall of the chamber 110.

Figure 13:
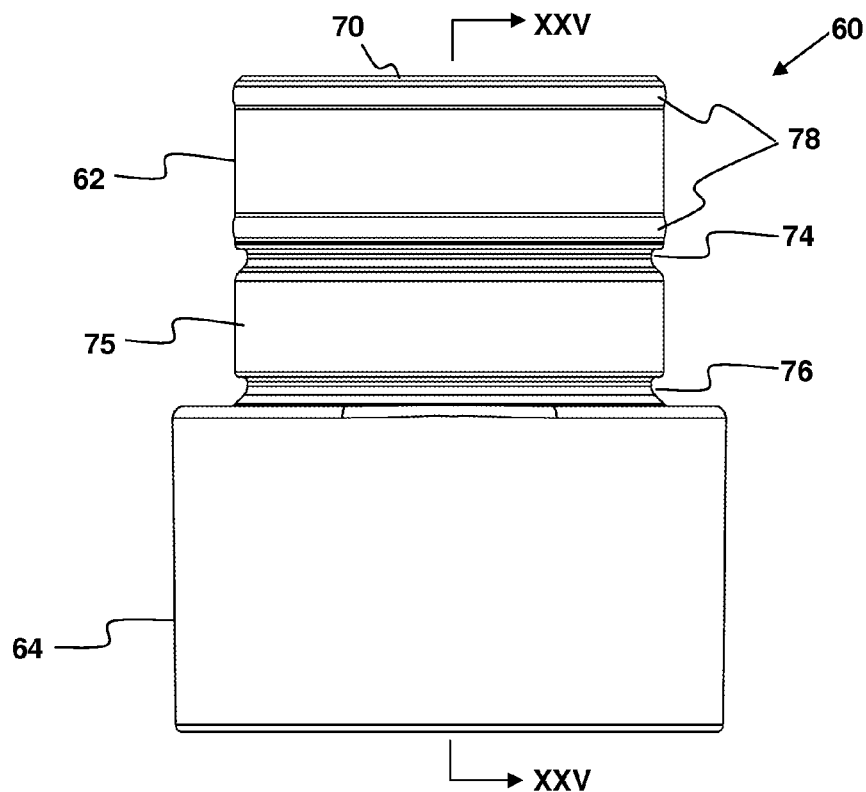
FIG. 13 is a side view of a mouthpiece, which forms part of the delivery device.
Figure 14:
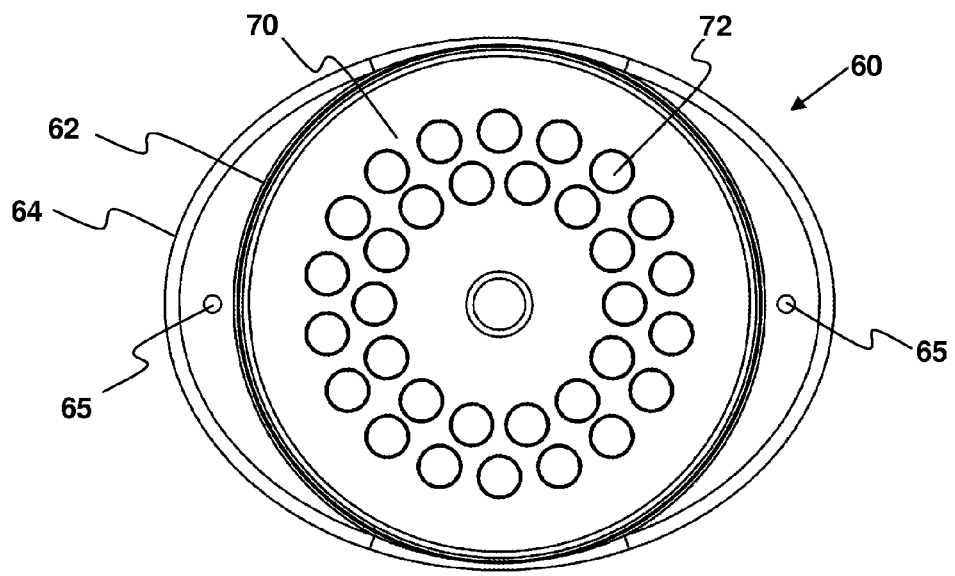
FIG. 14 is a plan view of the mouthpiece.
Figure 15:
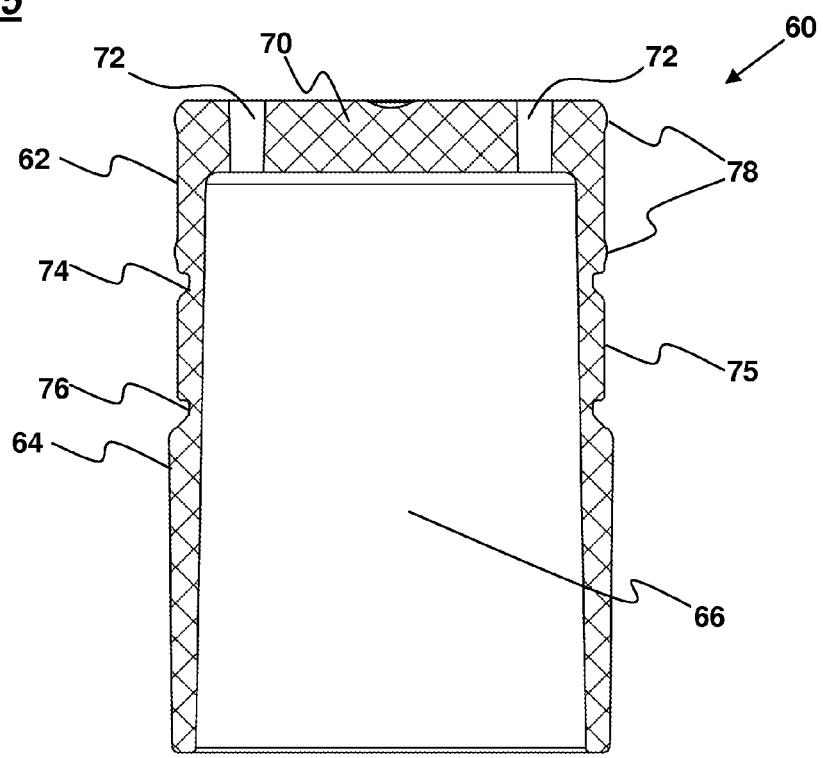
FIG. 15 is a cross-sectional view of the mouthpiece, along the line XXV-XXV in FIG. 13.

The mouthpiece 60 is shown in isolation, and in greater detail, in FIGS. 13 to 15. The mouthpiece 60 comprises a connection portion 62 and an outlet portion 64, which together define an inhalation passageway 66. In particular, the inhalation passageway 66 defined by the interior surfaces of the mouthpiece 60 has a generally circular cross-sectional shape, and a gradually increasing diameter as it extends to the end located in a patient's mouth, in use.

The connection portion 62 has an end wall 70, at an inner end of the mouthpiece 60, which defines an inlet to the inhalation passageway 60. In particular, the end wall 70 has the form of a circular disc, with thirty-two circular openings 72 formed therein. The circular openings 72 are arranged in two concentric circles at radii approximately midway between the centre of the end wall 70 and its outer edge. These circular openings 72 provide fluid communication between the chamber 110 and the inhalation passageway 66 of the mouthpiece 60, when the delivery device 100 is in its operative configuration.

The connection portion 62 has a substantially circular cross-section, and an external diameter substantially equal to the internal diameter of the sleeve 32 of the body 20. In particular, the connection portion 62 of the mouthpiece 60 is slidably mounted within the sleeve 32 of the body 20, as illustrated in FIGS. 1 to 4. However, the permitted movement of the mouthpiece 60 relative to the body 20 is restricted by corresponding grooves 74,76 and projections 36 formed on the mouthpiece 60 and body 20 respectively, as discussed in more detail below.

The outlet portion 64 of the mouthpiece 60 is arranged co-axially with the connection portion 62. The outlet portion 64 has a substantially elliptical outer wall, which is shaped to facilitate engagement with the mouth of a patient. The width of the outlet portion 64 is greater than the internal diameter of the sleeve 32. The outlet portion 64 of the mouthpiece 60 also has a substantially cylindrical inner wall, which together with the connection portion 62 defined the inhalation passageway 66 of the delivery device 100.

The inner and outer walls of the outlet portion 64 are joined on the minor axis of the elliptical outer wall, but are separated to each side of that axis, such that two auxiliary gas passageways are defined on each side of the inhalation passageway 66 in the outlet portion 64 of the mouthpiece 60. These two auxiliary gas passageways are open at the outer end of the mouthpiece 60, through which the patient inhales, but are substantially closed at the other end of the outlet portion 64 of the mouthpiece 60 by end walls that join the inner and outer walls of the outlet portion 64. A small bleed hole 65 is formed in each of these end walls, at the end of each auxiliary gas passageway, such that the patient draws some atmospheric air into the mouthpiece 60 during inhalation.

The external surface of the connection portion 62 of the mouthpiece 60 includes inner and outer circumferential grooves 74, 76. An outer groove 76 is disposed adjacent to the outlet portion 64 of the mouthpiece 60, and an inner groove 74 is disposed approximately midway between the end wall 70 and the outlet portion 64 of the mouthpiece 60. The connection portion 62 of the mouthpiece 60 is received within the sleeve 32, with the inwardly extending projections 36 of the sleeve 32 engaging one of the grooves 74, 76 with a snap fit, depending on whether the delivery device 100 is in its pre-use or operative configuration, which retains the mouthpiece 60 in place within the sleeve 32.

As shown clearly in FIG. 15, the grooves 74, 76 have a chamber-side wall that is orientated generally perpendicularly to the longitudinal axis of the mouthpiece 60, and its direction of movement, in use, and an outlet-side wall that is inclined relative to the chamber-side wall. As shown in FIGS. 2, 4 and 9, the corresponding projections 36 of the body 20 have a similar shape.

As shown clearly in FIGS. 2 and 4, the projections 36 at the end of the sleeve 34 of the body 20 are received within the inner groove 74 of the mouthpiece 60, with a snap fit, when the mouthpiece 60 is in its pre-use position. In this configuration, the end wall 70 of the mouthpiece 60 is set back from the annular support 22 of the body 20, such that the lower surface of the chamber 110 comprises a generally cylindrical recess defined by an inner portion of the sleeve 32 and the end wall 70 of the mouthpiece 60.

In this pre-use configuration, the inner groove 74 and the projections 36 are configured to prevent movement of the mouthpiece 60 away from the body 20, and hence prevent removal of the mouthpiece 60 from the delivery device 100. However, the inner groove 74 and the projections 36 are configured to enable movement of the mouthpiece 60 towards the body 20, until the projections 36 of the sleeve 32 are received, with a snap fit, within the outer groove 76 of the mouthpiece 60, such that the mouthpiece 60 is in its operative position.

In use, the mouthpiece 60 is deployed from the pre-use position to the operative position by pressing the mouthpiece 60 into the sleeve 32 with sufficient force to overcome the snap fit between the inner groove 74 and the projections 36. The force required to overcome this snap fit is sufficiently high that the risk of accidental deployment of the mouthpiece 60 is low, but is sufficiently low that the mouthpiece 60 can be reasonably moved by hand.

The notches 38 located in the sleeve 32 on both sides of each projection 36 allow the projections 36 to be urged outwardly during deployment of the mouthpiece 60, without deformation of the remainder of the sleeve 32. Once the snap fit is disengaged, as discussed above, the mouthpiece 60 is able to travel further into the sleeve 32 until the projections 36 engage the outer groove 76 with a snap fit, locking the mouthpiece 60 in the operative position. The snap fit between the outer groove 76 and the projections 36 does not allow the mouthpiece 60 to be returned to the pre-use position, and the greater external diameter of the outlet portion 64 of the mouthpiece 60 prevents the mouthpiece 60 being pushed any further into the sleeve 32. The mouthpiece 60 is therefore securely locked in the operative position once the snap fit between the outer groove 76 and the projections 36 has been engaged.

In this operative configuration, the connection portion 62 of the mouthpiece 60 is entirely received within the sleeve 32 of the body 20, and the outlet portion 64 of the mouthpiece 60 is disposed adjacent to the end of the sleeve 32. In addition, the end wall 70 of the mouthpiece 60 is aligned with the annular support 22 of the body 20, such that these components define a substantially flat end wall of the chamber 110. In particular, the chamber 110 is substantially cylindrical in this configuration.

In addition, two circumferential ridges 78 extend around the external surface of the connection portion 62 between the inner groove 74 and the end of the mouthpiece 60. In particular, one of the circumferential ridges 78 is disposed at the end of the mouthpiece 60, and the other circumferential ridge 78 is disposed adjacent to the inner groove 74. These circumferential ridges 78 improve the seal against the interior surface of the sleeve 34 of the body 20 to reduce the risk of gas flow leakage into the chamber 110 of the delivery device 100 during use.

The container 80 is shown in isolation, and in greater detail, in FIGS. 20 to 25. The container 80 is substantially drum shaped, and comprises a cup portion 82 that is open at one end, and a lid 92 that closes the open end of the cup portion 82.

The cup portion 82 of the container 80 comprises an end wall 84 having a convex exterior surface, and a generally cylindrical side wall 86 that is open at one end. An inwardly extending ridge 88 is provided at the open end of the cup portion 82, extending from the interior surface of the side wall 86. Two slots 90 are also formed in the side wall 86, extending from the open end, on opposite sides of the cup portion 82.

The lid 92 of the container 80 has an end wall 94 with a convex exterior surface, and a peripheral skirt 96 that engages the inwardly extending ridge 88 of the cup portion 82 to connect the cup portion 82 and the lid 92 together. The skirt 96 partially obstructs the two slots 90 in the side wall 86 of the cup portion 82, when the container 80 is assembled, leaving a small opening 98 in each slot 90 from which powder is dispensed, in use, as discussed in more detail below.

Figure 26:
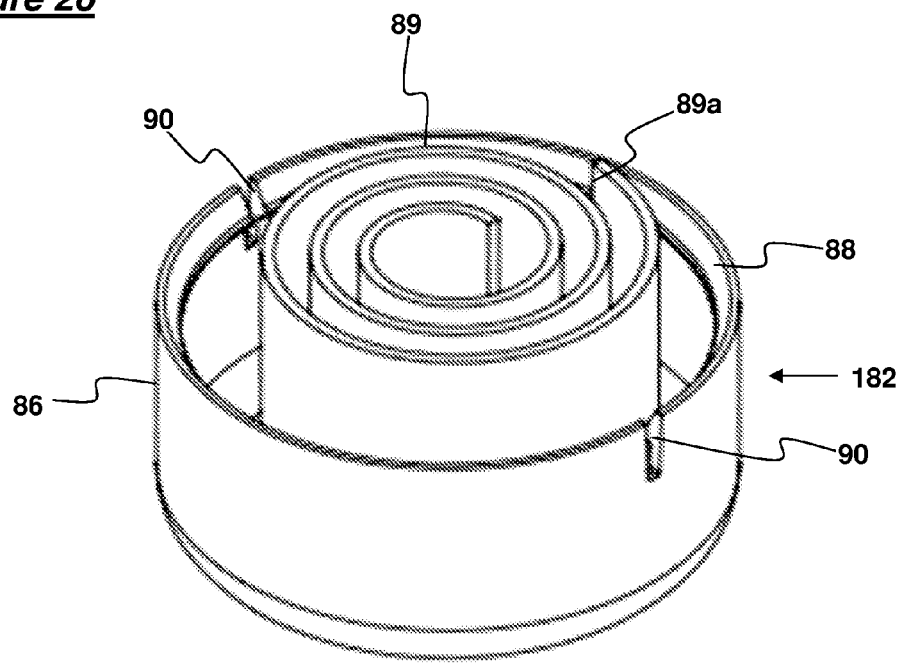
FIG. 26 is a perspective view of a second embodiment of the cup portion of a container.
Figure 27:
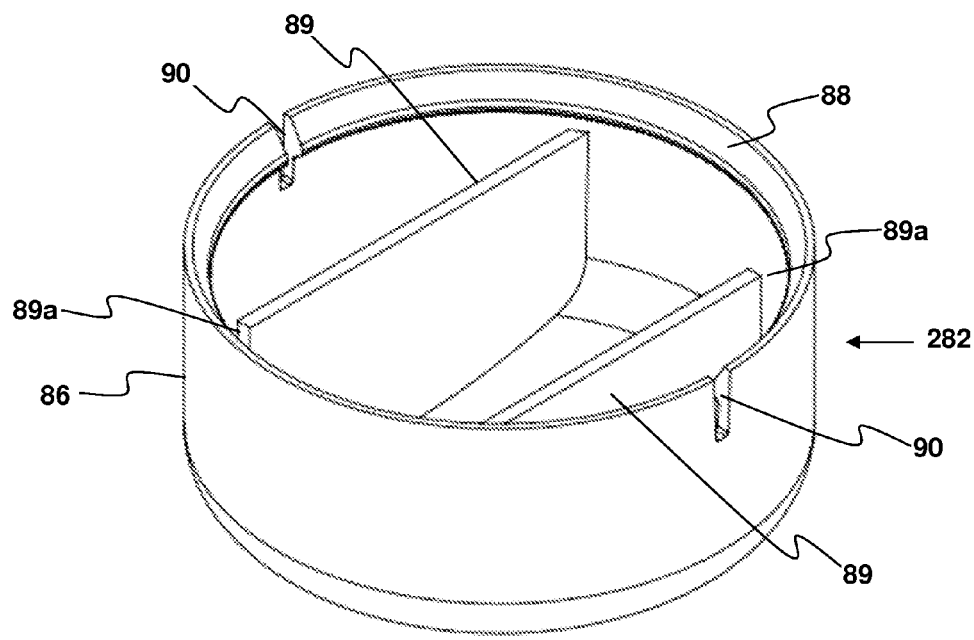
FIG. 27 is a perspective view of a third embodiment of the cup portion of a container.
Figure 28:
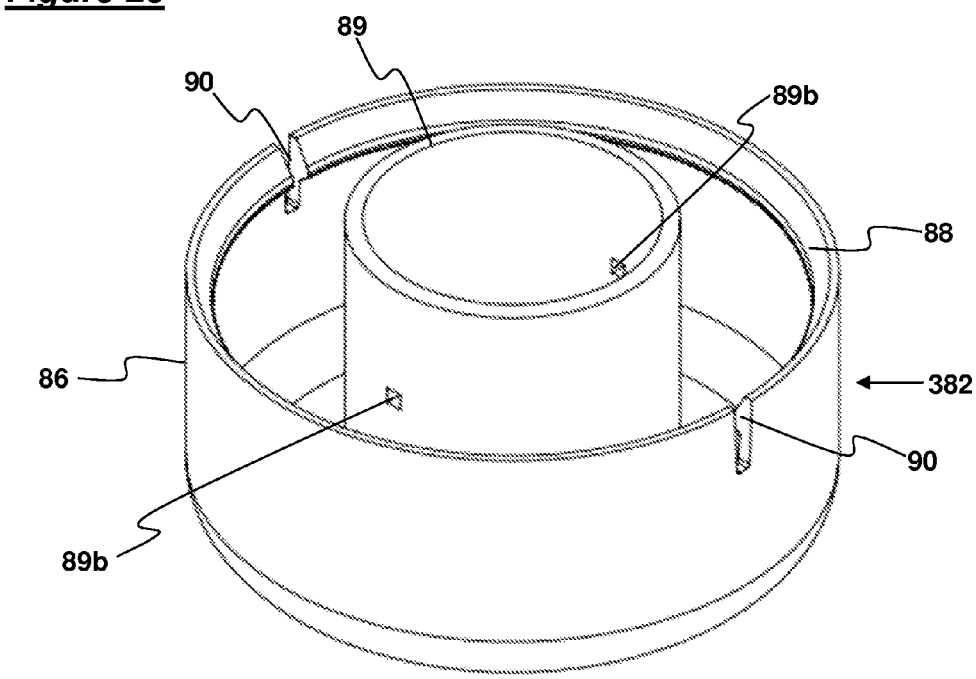
FIG. 28 is a perspective view of a fourth embodiment of the cup portion of a container.

Further embodiments of the cup portions 182, 282, 382 of containers 80 are shown in FIGS. 26 to 28, which comprise internal baffles 89 that divide the internal compartment of the container 80 into a number of sub-chambers. The baffles 89 include gaps 89a or openings 89b that allow restricted powder flow between these sub-chambers. The flow of powder within the container 80 while the delivery device 100 is operated is restricted by the baffles 89, such that powder emission from the openings 98 of the container 80 is restricted as the container 80 undergoes motion.

Figure 29:
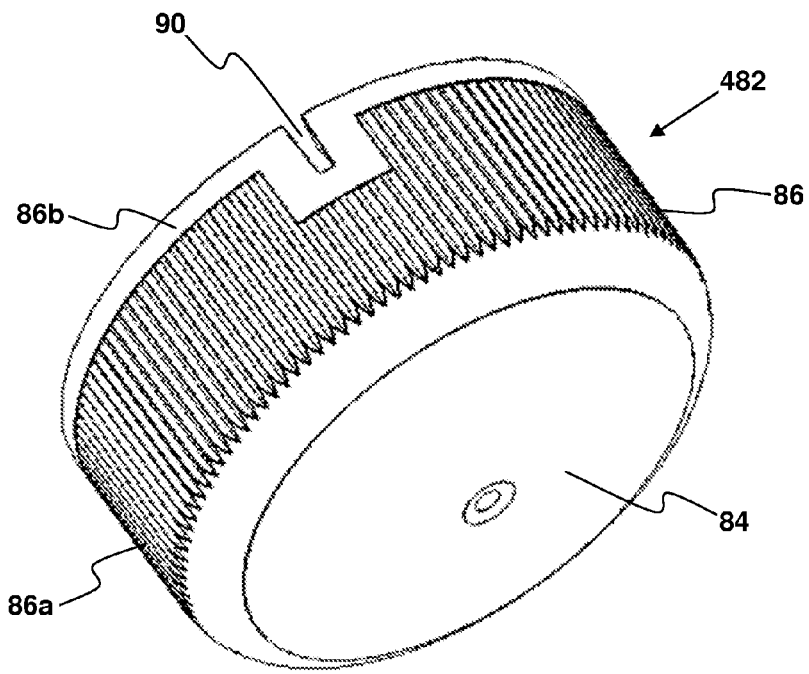
FIG. 29 is a perspective view of a fifth embodiment of the cup portion of a container.

Yet a further embodiment of the cup portion 482 of a container 80 is shown in FIG. 29, in which the side wall 86 comprises a textured portion 86a formed of a series of ribs, aligned with the cylindrical axis of the container 80. The textured portion 86a improves coupling between the container 80 and the gas flow through the chamber 110, which modifies the motion of the container 80 while the delivery device 100 is operated. The side wall 86 of the cup portion 482 also comprises a smooth portion 86b adjacent to the rim of the cup portion 482 and the slots 90, which allows effective sealing of the openings 98 and a secure interference fit with the internal surface of the sleeve 32 adjacent to the annular support 22.

The exterior diameter of the container 80 is substantially equal to the internal diameter of the sleeve 32, such that the container 80 is retained with an interference fit within the sleeve 32 in the pre-use configuration.

As shown clearly in FIG. 2, when the mouthpiece 60 is in its pre-use position, the container 80 is retained at least partially within the recess in the lower surface of the chamber 110 by an interference fit between the side wall 86 of the container 80 and internal surface of the end of the sleeve 32 adjacent the annular support 22. In this configuration, the lid 92 of the container 80 is in contact with the end wall 70 of the mouthpiece 60.

The interference fit between the container 80 and the interior surface of the sleeve 32 is sufficiently secure to prevent the container 80 becoming inadvertently dislodged, ie without movement of the mouthpiece 60 into the operative position. The engagement between the side wall 86 of the container 80 and the sleeve 32 also seals the openings 98 sufficiently to prevent any powder escaping from the container 80 in the pre-use configuration.

Figure 16:
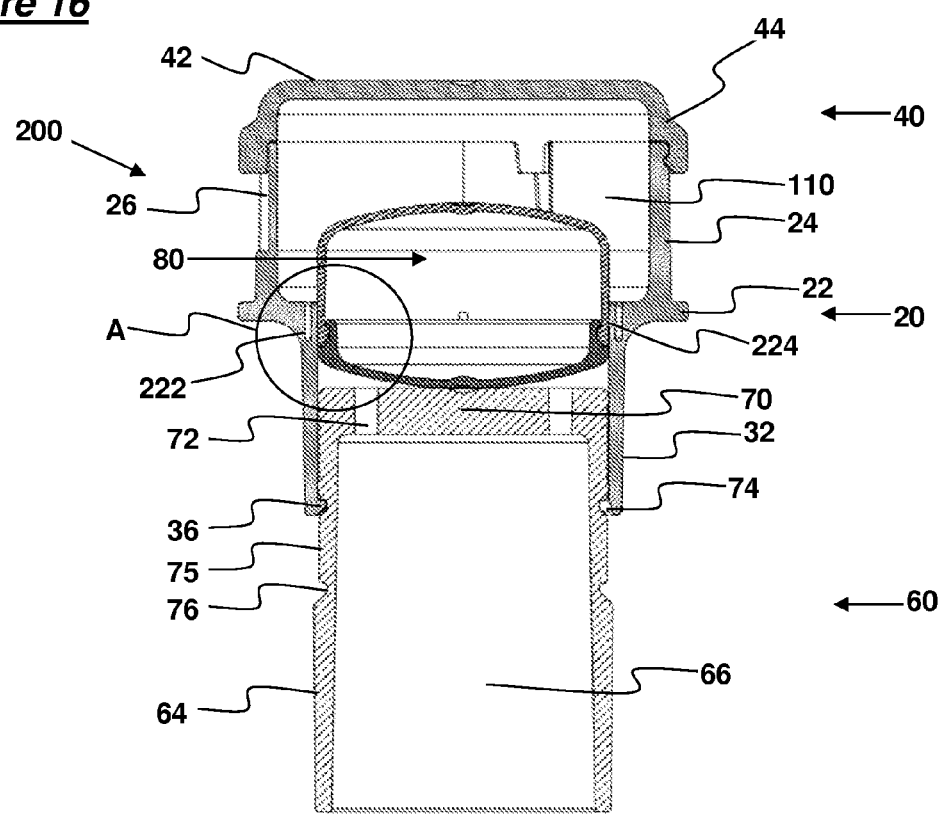
FIG. 16 is a cross-sectional view of a second embodiment of a delivery device according to this invention.
Figure 17:
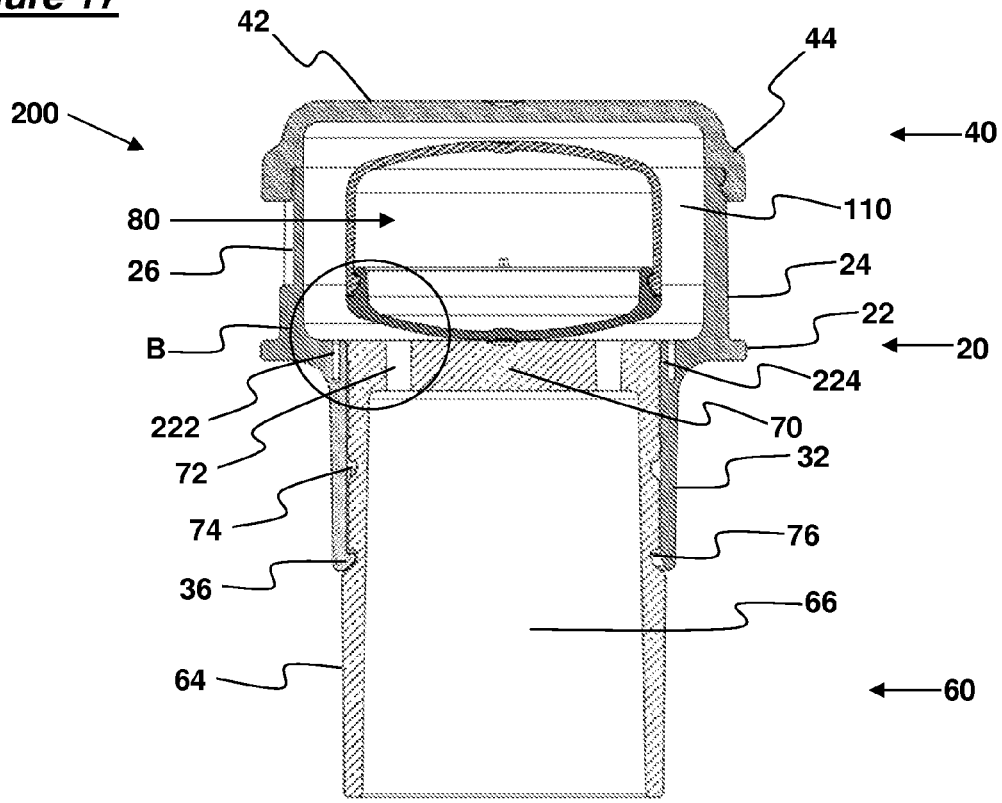
FIG. 17 is a cross-sectional view of the second embodiment of the delivery device in its operative configuration.

A second embodiment of a delivery device according to this invention, generally designated 200, is shown in a pre-use configuration in FIG. 16 and an operative configuration, in which the container 80 is deployed into a chamber 110, in FIG. 17. The second embodiment of the delivery device 200 is of essentially the same construction as the first embodiment 100, but further includes an annular groove 222 in the annular support 22 that circumscribes the opening at the upper end of the sleeve 32. The groove 222 defines a thin portion of material 224 of increased deformability around the rim of the opening at the upper end of the sleeve 32 that receives the container 80 while the delivery device 200 is in the pre-use configuration. The thin portion 224 comprises a ridge that extends into the opening at the upper end of the sleeve 32, such that this opening has a slightly reduced diameter around its rim. The rim of the opening at the upper end of the sleeve 32 is shown in greater detail in FIG. 18, in which the delivery device 200 is in the pre-use configuration, and in FIG. 19, in which the delivery device 200 is in the operative configuration.

Figure 18:
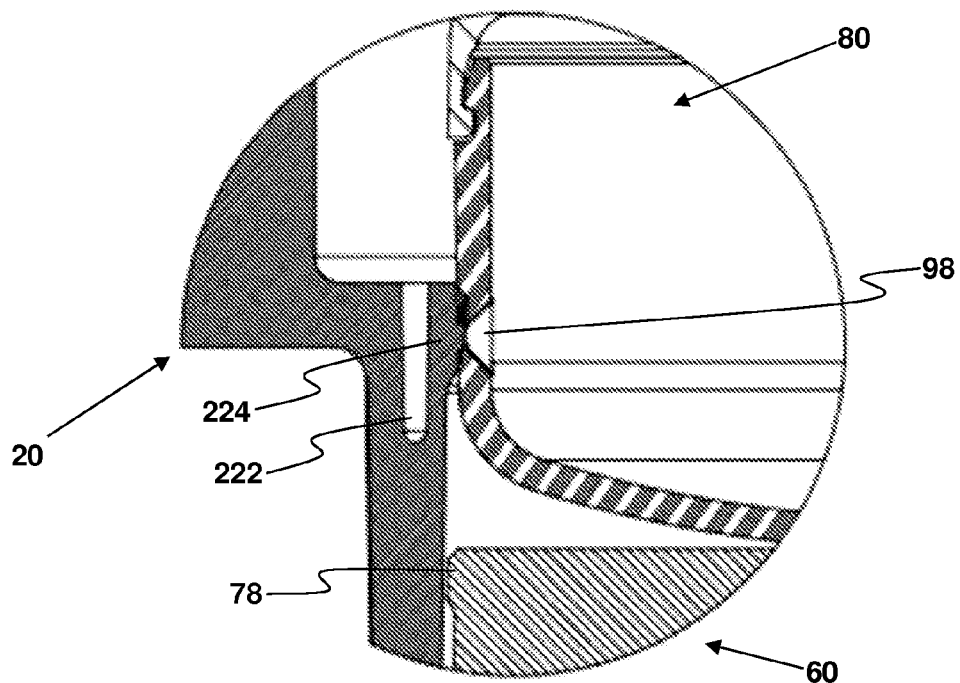
FIG. 18 is a close-up view of region A of FIG. 16.

When the delivery device 200 is in its pre-use configuration, the container 80 is retained in the opening at the upper end of the sleeve 32 by an interference fit between the side wall 86 of the container 80 and the inwardly extending ridge on the thin portion 224. The thin portion 224 is able to deflect into the groove 222, allowing it to accommodate small dimensional variations in the container 80, which are often encountered in high volume manufacturing. This arrangement improves sealing of the openings 98 and security of the interference fit between the side wall 86 of the container 80 and the sleeve 32 when the delivery device 200 is in its pre-use configuration. FIG. 18 shows a small overlap between the side wall 86 of the container 80 and the inwardly extending ridge on the thin portion 224, indicating the degree of interference between the container 80 and the thin portion 224.

Figure 19:
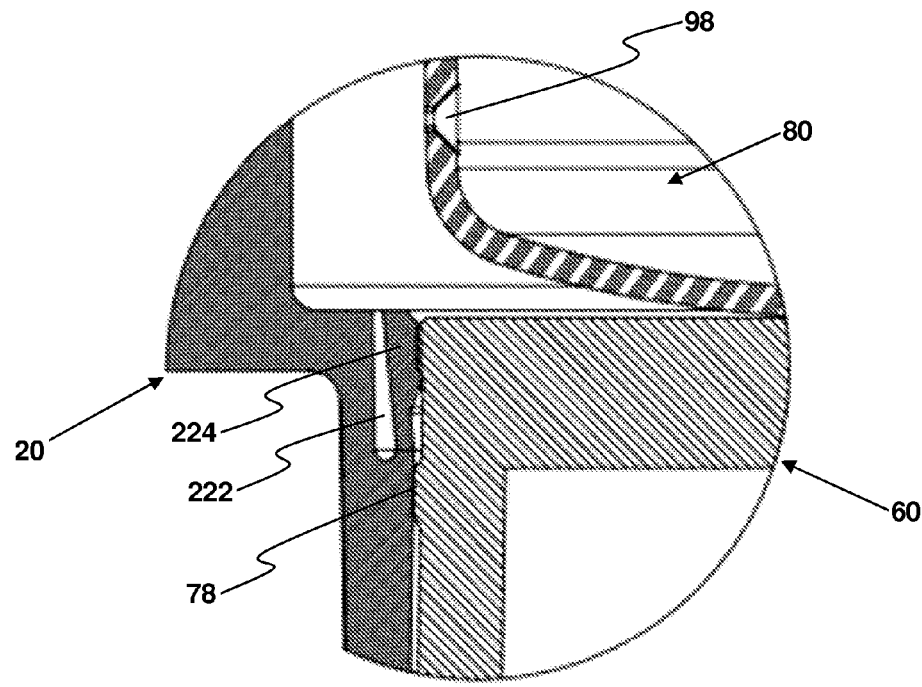
FIG. 19 is a close-up view of region B of FIG. 17.
Figure 20:
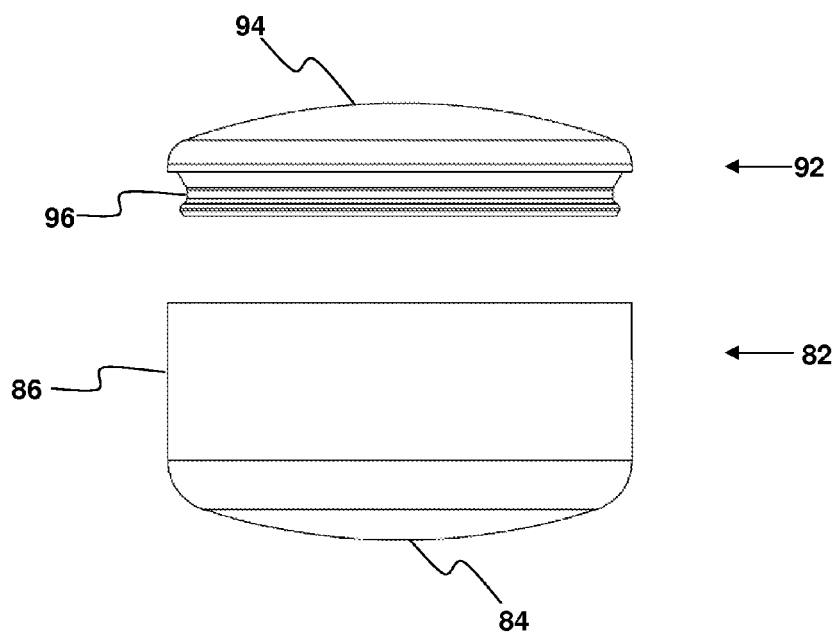
FIG. 20 is an exploded side view of a container, which forms part of the delivery device.
Figure 21:
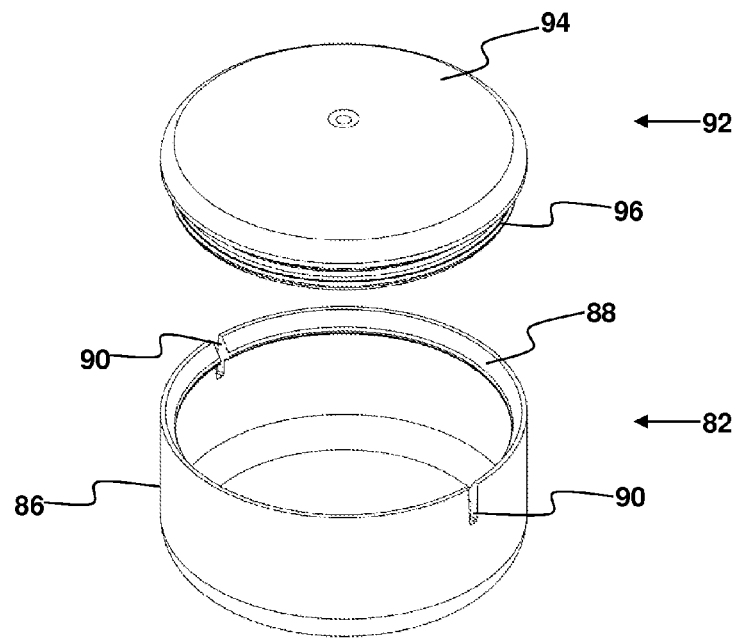
FIG. 21 is an exploded perspective view of the container.
Figure 22:
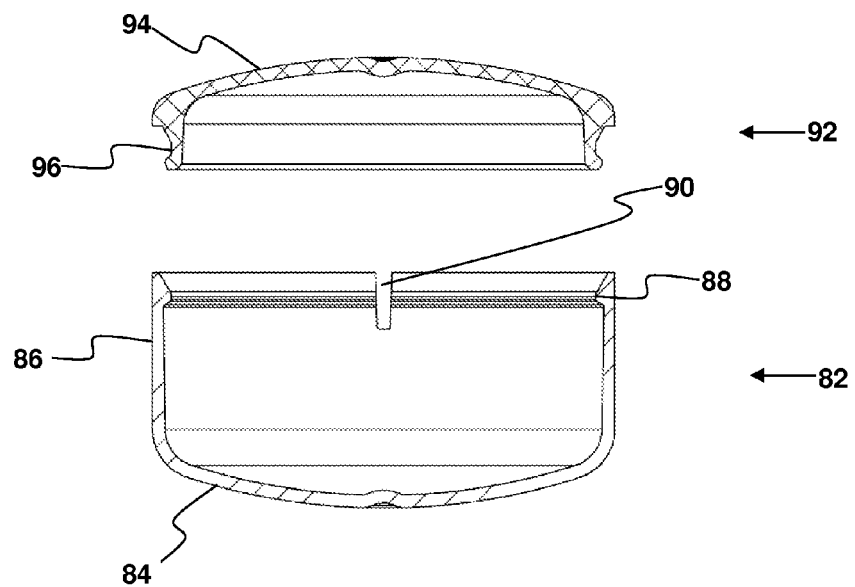
FIG. 22 is an exploded cross-sectional view of the container.
Figure 23:
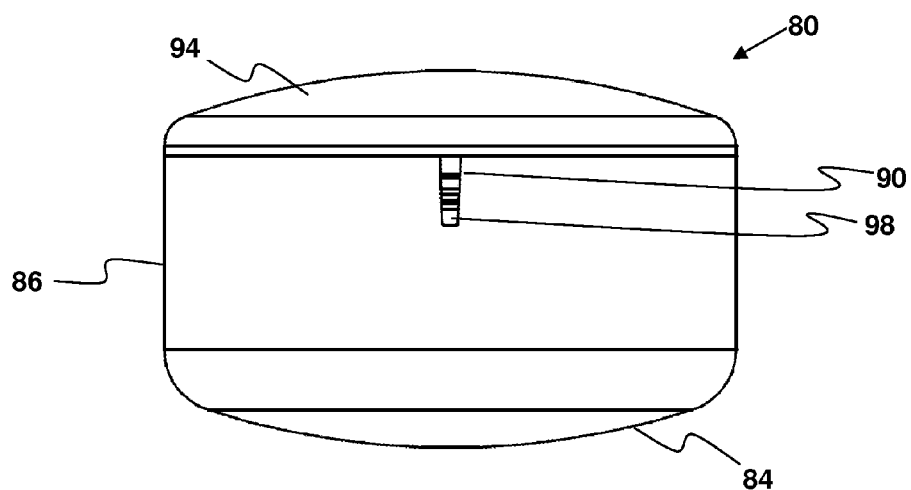
FIG. 23 is a side view of the container.
Figure 24:
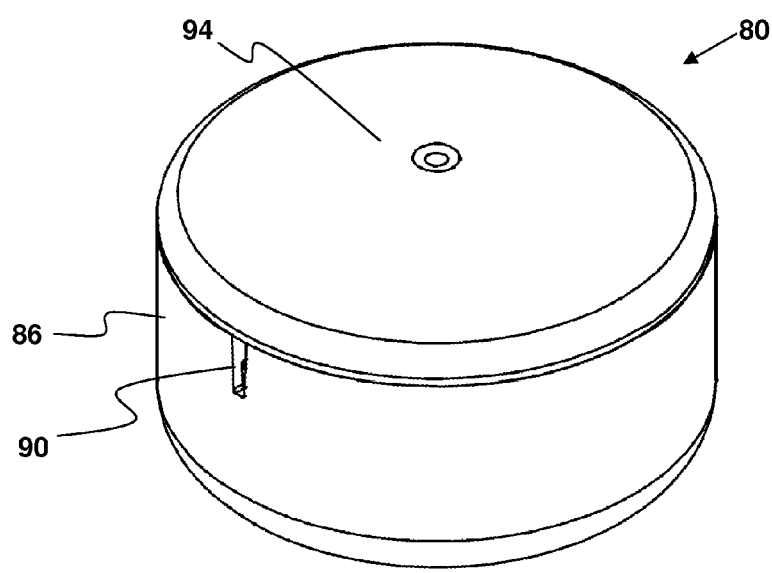
FIG. 24 is a perspective view of the container.
Figure 25:
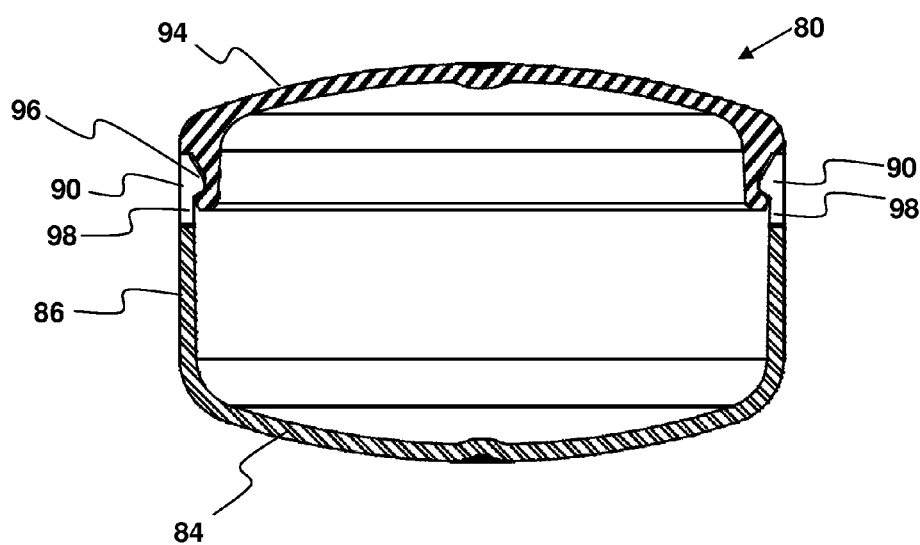
FIG. 25 a cross-sectional view of the container.

As the mouthpiece 60 is moved into the operative position, the circumferential ridge 78 located adjacent to the end wall 70 of the mouthpiece 60 contacts the inwardly extending ridge of the thin portion 224 causing the thin portion 224 to deflect outwardly into the groove 222, as shown in FIG. 19. Accordingly, when the mouthpiece 60 reaches the operative position with the end wall 70 aligned with the annular support 22, the thin portion 224 is deflected into the groove to such an extent that it closes off, or substantially closes off, the open end of the groove 222 from the chamber 110. The thin portion 224 retains this position during use, thereby preventing or substantially preventing the deposition of powder in the groove 222 while the delivery device is operated.

The delivery device 100 is stored, transported and supplied to the patient with the mouthpiece 60 in the pre-use position, as shown in FIG. 1, to prevent powder escaping from the container 80 prior to use. When the patient is ready to use the delivery device 100, the mouthpiece 60 is pressed into the operative position, which pushes the container 80 out of the recess, releasing it into the chamber 110 and unsealing the openings 98. The delivery device 100 is then ready to dispense powder.

The region of the external surface of the mouthpiece 60 that is located between then inner and outer grooves 74, 76 is colored to contrast with the other parts of the delivery device 100. The contrasting region 75 is visible when the mouthpiece 60 is in the pre-use position. However, when the mouthpiece 60 is deployed into the operative position, the contrasting region is hidden by the sleeve 32 and is no longer visible, providing a clear visual indication of when the mouthpiece 60 has been properly deployed and thus when the delivery device 100 is ready for use.

The delivery device 100 is operated by the patient inhaling through the outlet portion 64 of the mouthpiece 60. The elliptical cross-section of the outlet portion 64 of the mouthpiece 60 facilitates engagement with the mouth of a patient to reduce gas leakage at the corners of the mouth. Inhalation by the patient draws gas into the chamber 110 through the gas inlet slots 26. This gas exits the chamber 110 through the circular openings 72 in the end wall 70 of the mouthpiece 60, and flows into the inhalation passageway 66 of the mouthpiece 60, and then into the mouth and lungs of the patient.

The tangential arrangement of the gas inlet slots 26 causes gas drawn into the chamber 110 to be directed around its circumference, which generates a turbulent rotating body of gas within the chamber 110 that drives the motion of the container 80. The convex upper and lower surfaces of the container 80 reduce the contact area between the container 80 and the surface of the chamber 110, and also prevent the container 80 being sucked onto the end wall 70 of the mouthpiece 60, thereby allowing the container 80 to move more freely within the chamber 110. An effective sealing arrangement between the components 20, 40, 60 forming the chamber 110 prevents uncontrolled gas leakage into the chamber 110 that would produce additional turbulence and reduce the efficiency at which the gas flow within the chamber 110 causes the desired motion of the container 80.

Figure 30:
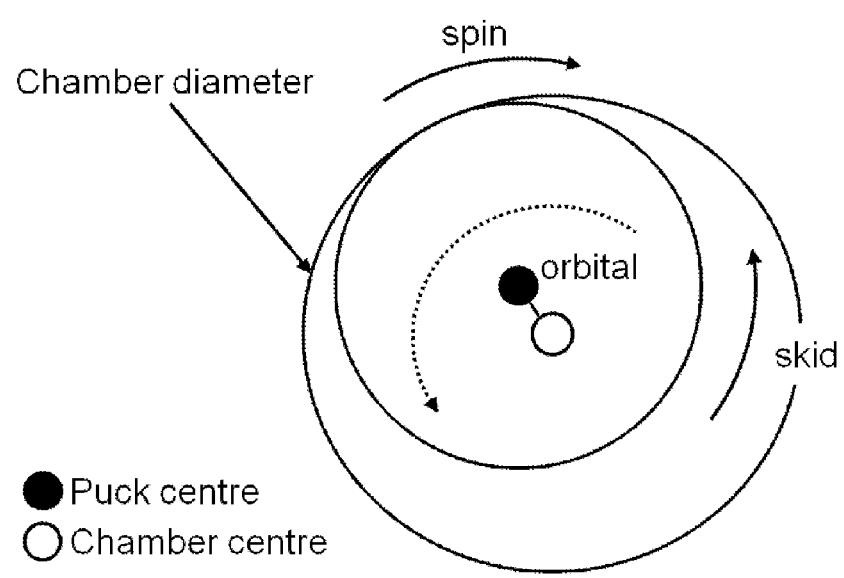
FIG. 30 is a diagrammatic representation of the motion of the container when the delivery device is in use.

In use, emission of the powder from the openings 98 in the container 80 is brought about by motion of the container 80 within the chamber 110. This motion is illustrated in FIG. 30. The turbulent rotating body of gas in the chamber 110 drives the container 80 in an orbital motion around the central axis of the chamber 110, with the side wall 86 of the container 80 substantially remaining in contact with the circumferential wall of the chamber 110. This orbital motion is accompanied by rotation of the container 80 about its own axis, either in rolling contact with the circumferential wall of the chamber 110 in a substantially epicyclic fashion, or in a non-rolling direction, whereby the container 80 is skidding against the chamber wall. Motion of the container 80 generally includes both epicyclic and skidding motion. The balance between epicyclic and skidding motion is influenced by the ratio of the diameter of the container 80 to that of the chamber 110.

The chamber 110 has a diameter of 23 mm, relative to a diameter of 18 mm for the container 80. This configuration promotes epicyclic motion of the container 80, which is the most efficient form of motion for powder emission. This configuration may also provide enhanced milling of the emitted powder between the container 80 and the wall of the chamber 110 as the container 80 orbits the chamber 110, aiding deagglomeration of the powder.

The container 80 is designed to be as light as possible to maximise the mass of powder that can be driven with the available gas flow. The container 80 contains about 400 mg of powder, leaving a headspace comprising about 30% of the volume of the container 80. This headspace allows the powder to tumble within the container 80, improving emission of the powder from the openings 98 and further aiding deagglomeration.

Powder is emitted from the openings 98 continuously while the container 80 is undergoing motion, allowing the delivery device 100 to deliver a substantially steady amount of powder throughout each inhalation manoeuvre, reducing the likelihood of the patient experiencing a cough reaction.

Powder emitted from the container 80 is entrained in the turbulent rotating body of gas in the chamber 110, and this powder-laden gas is drawn through the openings 72 in the end wall 70 of the mouthpiece 60, into the inhalation passage 66. The openings 72 in the end wall 70 of the mouthpiece 60 act to reduce the rotational velocity of the powder-laden gas passing through it, such that the gas flow is substantially straightened once it enters the inhalation passageway 66, reducing powder deposition on the internal surface of the mouthpiece 60.

The bleed holes 65 located on opposite sides of the outlet portion 64 of the mouthpiece 60 provide an additional gas flow path into the mouthpiece 60, which bypasses the chamber 110 and reduces the resistance of the delivery device 100. The gas entering the bleed holes 65 is atmospheric air that does not contain entrained powder, and so can shield the powder-laden gas from the mouth and throat of the patient and prevent it from entering the auxiliary gas passageways, reducing powder deposition in these areas.

Administration of the full 400 mg dose requires a number of sequential inhalations by the patient. The number of inhalations required is typically between five and eight but may be more or less.

EXAMPLE

Emitted Dose (ED) and Fine Particle Dose (FPD) Testing

Three delivery devices substantially as described above were provided, one having a chamber 22 mm in diameter, one with a chamber 23 mm in diameter and the last with a chamber 24 mm in diameter.

All containers used were 18 mm in diameter and had a single exit orifice with a cross-sectional area of around 0.18 $mm^2$. The containers contained 400 mg±3 mg of mannitol formulated as a dry respirable powder.

The Emitted Dose (ED) and Fine Particle Dose (FPD) produced by each delivery device was tested using a standard Multistage Liquid Impinger (MSLI).

Each delivery device was loaded with a container and a gas flow of between 50 and 55 liters/min was drawn through the chamber in shots of around 4 seconds until the powder emission rate became negligible, generally after between 5 and 10 shots. This process was repeated several times for each delivery device.

The ED for each delivery device was calculated directly from the powder emission results produced by the MSLI. FPD was calculated with Copley Inhaler Testing Data Analysis Software (CITDAS) from powder emission results produced by the MSLI. The ED and FPD of each device are shown in Table 1.

TABLE 1

Emitted Dose (ED) and Fine Particle Dose (FPD) produced by delivery devices of various chamber diameters

| Device | Emitted Dose (ED) | | Fine Particle Dose (FPD) | |
| --- | --- | --- | --- | --- |
| | Mean | Range | Mean | Range |
| 22 mm Chamber | 335.8 | 313 to 347 | 131.6 | 128 to 135 |
| 23 mm Chamber | 346.3 | 338 to 352 | 131.0 | 115 to 146 |
| 24 mm Chamber | 351.9 | 350 to 354 | 131.1 | 118 to 139 |

The invention claimed is:

1. A delivery device comprising:
 a container containing a dose of powder and having a preformed opening;
 a chamber adapted to receive the container;
 at least one gas inlet in a side wall of the chamber by which gas may enter the chamber;
 at least one gas outlet by which gas and entrained powder may exit the chamber for inhalation;
 a sleeve extending from an end of the side wall of the chamber and having an opening into the chamber; and
 a deployment member configured to move the delivery device from a pre-use configuration to an operative configuration, wherein:
  in the pre-use configuration, the container is accommodated, at least partially, within the sleeve and the deployment member has an end wall positioned within the sleeve;
  the deployment member adapted to put the delivery device in the operative configuration by displacing, with the end wall, the container from the sleeve into the chamber, such that all of the container is released into the chamber with the end wall positioned in the opening into the chamber in the operative configuration to form a surface of the chamber;
  the container being a free standing structure with a central axis, the container being freely movable within the chamber in the operative configuration by gas flow generated by the inhalation of a patient or by gas flow generated by a gas source, releasing the powder through the preformed opening with the container remaining intact in the operative configuration; and
  the at least one gas inlet is positioned so that, in use, the gas flow in the chamber drives the central axis of the container in an orbital motion around a central axis of the chamber while a perimeter of the container always surrounds the central axis of the chamber.

2. The delivery device as claimed in claim 1, wherein the deployment member is movably mounted relative to the chamber, such that the end wall of the deployment member contacts the container in the sleeve in the pre-use configuration, and urges the container into the chamber on movement from the pre-use configuration to the operative configuration.

3. The delivery device as claimed in claim 1, wherein the deployment member is retained in the pre-use configuration by retaining formations adapted to maintain the deployment member in the pre-use configuration during normal handling.

4. The delivery device as claimed in claim 1, wherein an entire length of the sleeve is occupied by the deployment member in the operative configuration such that the gas flow within the chamber, in use, is not adversely affected by the presence of a void space within the sleeve.

5. The delivery device as claimed in claim 1, wherein the deployment member is retained in the operative configuration by retaining formations.

6. The delivery device as claimed in claim 5, wherein the retaining formations have the form of a cooperating projection and recess.

7. The delivery device as claimed in claim 5, wherein the delivery device is a single-use, disposable device, and the retaining formations are adapted to prevent further movement of the deployment member, without damaging the delivery device.

8. The delivery device as claimed in claim 1, wherein the deployment member defines at least part of an inhalation passageway of the delivery device, through which gas and entrained powder are inhaled by a patient.

9. The delivery device as claimed in claim 8, wherein the inhalation passageway defined by the deployment member extends from the end wall in which the at least one gas outlet is formed.

10. The delivery device as claimed in claim 8, wherein the deployment member also comprises a mouthpiece or a nosepiece, through which gas and entrained powder are withdrawn from the delivery device, in the operative configuration.

11. The delivery device as claimed in claim 1, wherein a seal is formed between an exterior surface of the deployment member and an interior surface of the sleeve, such that gas and entrained powder does not leak into the sleeve during use.

12. The delivery device as claimed in claim 1, wherein the deployment member is moveably mounted within the sleeve, and the deployment member is received within the sleeve to a greater extent in the operative configuration, relative to the pre-use configuration.

13. The delivery device as claimed in claim 12, wherein the deployment member includes indications that are visible in the pre-use configuration, and hidden in the operative configuration by the sleeve, in order to indicate a status of the delivery device.

14. The delivery device as claimed in claim 1, wherein the container is compliant.

15. The delivery device as claimed in claim 1, wherein an interior surface of the sleeve comprises a resilient portion.

16. The delivery device as claimed in claim 1, wherein the container comprises one or more additional preformed openings for dispensing the dose from the container.

17. The delivery device as claimed in claim 1, wherein the container is formed of a number of cooperating components, wherein the preformed opening is defined between the cooperating components.

18. The delivery device as claimed in claim 1, wherein the preformed opening is integrally formed with the container.

19. The delivery device as claimed in claim 1, wherein the preformed opening is closed by a closure member in the pre-use configuration.

20. A method of delivering a powder, comprising using the delivery device as claimed in claim 1.

21. A method of treatment of a patient with a respiratory disorder, comprising administering at least one powdered medicament using the delivery device as claimed in claim 1.

22. The delivery device as claimed in claim 1, wherein the at least one gas inlet comprises a tangential arrangement of at least one gas inlet slot causing gas drawn into the chamber to be directed around a circumference of the chamber such that the gas flow comprises a rotating body of gas within the chamber that drives the motion of the container.

23. The delivery device as claimed in claim 1, wherein the orbital motion is accompanied by rotation of the container about its central axis.

24. A delivery device comprising:
 a discrete container containing a dose of powder and having a preformed opening;
 a chamber adapted to receive the container;
 at least one gas inlet in a side wall of the chamber by which gas may enter the chamber;
 at least one gas outlet by which gas and entrained powder may exit the chamber for inhalation;
 a sleeve extending from the chamber; and
 a deployment member accommodated in the sleeve through an end of the sleeve opposite the chamber, wherein:
  in a pre-use configuration, an end wall of the deployment member is positioned within the sleeve between a distal end of the sleeve and a chamber end of the sleeve and is in contact with the container;
  in an operative configuration, the end wall of the deployment member is positioned flush with a chamber end of the sleeve, such that all of the container is released into the chamber, to form a surface of the chamber within which the container is confined;
  the container being a free-standing structure with a central axis, the at least one gas inlet positioned so that, in use, the gas flow in the chamber drives the central axis of the container in an orbital motion around a central axis of the chamber while a perimeter of the container always surrounds the central axis of the chamber.

25. The delivery device as claimed in claim 24, wherein the deployment member is retained in the pre-use configuration by retaining formations adapted to enable movement of the deployment member into the operative configuration, but prevent other movement, without damaging the delivery device.

* * * * *